(12) United States Patent
Ballinger et al.

(10) Patent No.: US 9,592,306 B2
(45) Date of Patent: Mar. 14, 2017

(54) MITOCHONDRIAL-NUCLEAR EXCHANGED CELLS, TISSUES, ORGANS AND ANIMALS

(71) Applicant: THE UAB RESEARCH FOUNDATION, Birmingham, AL (US)

(72) Inventors: Scott Webster Ballinger, Odenville, AL (US); Danny R. Welch, Shawnee, KS (US); Robert Allen Kesterson, Birmingham, AL (US); Larry W. Johnson, Jasper, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/697,243

(22) Filed: Apr. 27, 2015

(65) Prior Publication Data

US 2015/0231278 A1 Aug. 20, 2015

Related U.S. Application Data

(63) Continuation of application No. 13/360,344, filed on Jan. 27, 2012, now Pat. No. 9,040,771, which is a continuation of application No. 12/486,375, filed on Jun. 17, 2009, now abandoned.

(60) Provisional application No. 61/076,260, filed on Jun. 27, 2008.

(51) Int. Cl.
| | |
|---|---|
| *A61D 19/04* | (2006.01) |
| *A61K 49/00* | (2006.01) |
| *A01K 67/027* | (2006.01) |
| *G01N 33/50* | (2006.01) |

(52) U.S. Cl.
CPC ...... *A61K 49/0008* (2013.01); *A01K 67/0275* (2013.01); *A61D 19/04* (2013.01); *G01N 33/5023* (2013.01); *A01K 2227/105* (2013.01); *A01K 2267/0331* (2013.01); *A01K 2267/0375* (2013.01)

(58) Field of Classification Search
CPC ............... A61D 19/04; A01K 2207/00; A01K 2207/30; A01K 2217/00; A01K 2267/00; A01K 2267/0306; A01K 2267/035
USPC ............................................ 800/8, 9, 21, 24
See application file for complete search history.

(56) References Cited

U.S. PATENT DOCUMENTS

| 5,057,420 | A | 10/1991 | Massey et al. |
|---|---|---|---|
| 6,603,059 | B1 | 8/2003 | Strelchenko et al. |
| 7,361,804 | B1 | 4/2008 | Campbell et al. |
| 2003/0032180 | A1 | 2/2003 | Strelchenko et al. |
| 2004/0107454 | A1 | 6/2004 | Wheeler et al. |
| 2005/0095704 | A1 | 5/2005 | Robl et al. |
| 2005/0120402 | A1* | 6/2005 | St. John ............... C12N 15/873 800/21 |
| 2005/0250203 | A1 | 11/2005 | Robl et al. |
| 2006/0236416 | A1* | 10/2006 | Nagao ................. A01K 67/0273 800/18 |

FOREIGN PATENT DOCUMENTS

| WO | 9003432 | 4/1990 |
|---|---|---|
| WO | 9424274 | 10/1994 |
| WO | 9426884 | 11/1994 |

OTHER PUBLICATIONS

Sato et al, PNAS 102(46):16765-16770, 2005.*
Hayashi et al, PNAS 88:10614-10618, 1991.*
U.S. Appl. No. 13/360,344, "Final Office Action", May 31, 2013, 11 pages.
U.S. Appl. No. 13/360,344, "Final Office Action", Aug. 12, 2014, 8 pages.
U.S. Appl. No. 13/360,344, "Non-Final Office Action", Dec. 16, 2013, 5 pages.
U.S. Appl. No. 13/360,344, "Notice of Allowance", Jan. 26, 2015, 13 pages.
Adelroth et al., "Surface proton donors for the D-pathway of cytochrome c oxidase in the absence of subunit III", Biochemistry 45.27 (2006): 8308-8318.
Alexander et al., "Distinct phenotypes of obesity-prone AKR/J, DBA2J and C57BL/6J mice compared to control strains", International journal of obesity 30.1 (2006): 50-59.
Alexander, "Atherosclerosis as disease of redox-sensitive genes", Transactions of the American Clinical and Climatological Association 109 (1998): 129.
Alexander, "Hypertension and the pathogenesis of atherosclerosis oxidative stress and the mediation of arterial inflammatory response: a new perspective", Hypertension 25.2 (1995): 155-161.
Anderson et al., "Sequence and organization of the human mitochondrial genome", Nature 290.5806 (1981): 457-465.
Andrews et al., "Reanalysis and revision of the Cambridge reference sequence for human mitochondrial DNA", Nature genetics 23.2 (1999): 147-147.
Ballinger et al., "Hydrogen peroxide causes significant mitochondrial DNA damage in human RPE cells", Experimental eye research 68.6 (1999): 765-772.
Ballinger et al., "Maternally transmitted diabetes and deafness associated with a 10.4 kb mitochondrial DNA deletion", Nature genetics 1.1 (1992): 11-15.
Ballinger et al., "Mitochondrial diabetes revisited", Nature genetics 7.4 (1994): 458-459.
Ballinger et al., "Mitochondrial influence on breast cancer metastasis suscenptibility", Era of Hope, Department of Defense Breast Cancer Research Program, BC063079:Abstract, Jun. 16, 2008.
Ballinger et al., "Mitochondrial integrity and function in atherogenesis", Circulation 106.5 (2002): 544-549.

(Continued)

*Primary Examiner* — Kevin Hill
(74) *Attorney, Agent, or Firm* — Kilpatrick Townsend & Stockton LLP

(57) ABSTRACT

Provided herein are mitochondrial-nuclear exchanged cells and animals comprising mitochondrial DNA (mtDNA) from one subject and nuclear DNA (nDNA) from a different subject. Methods for producing a mitochondrial-nuclear exchanged animal and animals made by the methods are provided. Also provided are methods of screening for agents useful for treating a disease or disorder using mitochondrial-nuclear exchanged animals or cells, tissues or organs thereof.

7 Claims, 15 Drawing Sheets

(56) References Cited

OTHER PUBLICATIONS

Bandelt et al., "Median-joining networks for inferring intraspecific phylogenies", Molecular biology and evolution 16.1 (1999): 37-48.
Bandelt et al., "Mitochondrial portraits of human populations using median networks", Genetics 141.2 (1995): 743-753.
Bandelt et al., "The fingerprint of phantom mutations in mitochondrial DNA data", The American Journal of Human Genetics 71.5 (2002): 1150-1160.
Bartalesi et al., "Different lung responses to cigarette smoke in two strains of mice sensitive to oxidants", European Respiratory Journal 25.1 (2005): 15-22.
Berliner et al., "Atherosclerosis: basic mechanisms oxidation, inflammation, and genetics", Circulation 91.9 (1995): 2488-2496.
Berliner et al., "The role of oxidized lipoproteins in atherogenesis", Free Radical Biology and Medicine 20.5 (1996): 707-727.
Brown et al., "Clustering of Caucasian Leber hereditary optic neuropathy patients containing the 11778 or 14484 mutations on an mtDNA lineage", American journal of human genetics 60.2 (1997): 381.
Brown et al., "Novel mtDNA mutations and oxidative phosphorylation dysfunction in Russian LHON families", Human genetics 109.1 (2001): 33-39.
Brown et al., "The role of mtDNA background in disease expression: a new primary LHON mutation associated with Western Eurasian haplogroup J.", Human genetics 110.2 (2002): 130-138.
Cadenas et al., "Analysis of the pathways of nitric oxide utilization in mitochondria", Free radical research 33.6 (2000): 747-756.
Cai et al., "Endothelial dysfunction in cardiovascular diseases: the role of oxidant stress", Circulation research 87.10 (2000): 840-844.
Campbell et al., "Production of live lambs following nuclear transfer of cultured embryonic disc cells", Theriogenology 1.43 (1995): 181.
Carpenter et al., "Evidence of lipid oxidation in pulmonary artery atherosclerosis", Atherosclerosis 118.1 (1995): 169-172.
Chagnon et al., "Phylogenetic analysis of the mitochondrial genome indicates significant differences between patients with Alzheimer disease and controls in a French-Canadian founder population", American journal of medical genetics 85.1 (1999): 20-30.
Collas et al., "Nuclear transplantation by microinjection of inner cell mass and granulosa cell nuclei", Molecular reproduction and development 38.3 (1994): 264-267.
Corral-Debrinski et al., "Association of mitochondrial DNA damage with aging and coronary atherosclerotic heart disease", Mutation Research/DNAging 275.3 (1992): 169-180.
Dansky et al., "Genetic background determines the extent of atherosclerosis in ApoE-deficient mice", Arteriosclerosis, thrombosis, and vascular biology 19.8 (1999): 1960-1968.
Debenedictis et al., "Mitochondrial DNA inherited variants are associated with successful aging and longevity in humans", The FASEB Journal 13.12 (1999): 1532-1536.
Dhalla et al., "Role of oxidative stress in cardiovascular diseases", Journal of hypertension 18.6 (2000): 655-673.
Diaz et al., "Mechanisms of disease-antioxidants and atherosclerotic heart disease", New England Journal of Medicine 337.6 (1997): 408-416.
Eggan et al., "Mammalian and avian transgenesis—new approaches", (Pease, Shirley, and Carlos Lois, eds.) Springer Verlag, Heidelberg, Germany, pp. 41-96, 2006.
Evans et al., "Mitochondrial DNA genotypes in nuclear transfer-derived cloned sheep", Nature genetics 23.1 (1999): 90-93.
Ferrieres et al., "G030: Influence of parental history of cardiovascular risk factors on multiple metabolic syndrome", American Journal of Hypertension 13.S2 (2000): 263A.
Forman et al., "Superoxide radical and hydrogen peroxide in mitochondria", Free radicals in biology 5 (1982): 65-90.
Freeman et al., "Oxygen radical-nitric oxide reactions in vascular diseases", Advances in Pharmacology 34 (1995): 45-69.
Gokcumen et al., "Genetic variation in the enigmatic Altaian Kazakhs of South-Central Russia: Insights into Turkic population history", American journal of physical anthropology 136.3 (2008): 278-293.
Gonder et al., "Whole-mtDNA genome sequence analysis of ancient African lineages", Molecular biology and evolution 24.3 (2007): 757-768.
Goto et al., "A mutation in the tRNALeu (UUR) gene associated with the MELAS subgroup of mitochondrial encephalomyopathies", Nature, 348: 651-653, 1990.
Halliwell, "Free radicals, reactive oxygen species and human disease: a critical evaluation with special reference to atherosclerosis", British journal of experimental pathology 70.6 (1989): 737.
Harrison et al., "Role of oxidative stress in atherosclerosis", The American journal of cardiology 91.3 (2003): 7-11.
Hazen et al., "3-Chlorotyrosine, a specific marker of myeloperoxidase-catalyzed oxidation, is markedly elevated in low density lipoprotein isolated from human atherosclerotic intima", The Journal of clinical investigation 99.9 (1997): 2075.
Herrnstadt et al., "Reduced-median-network analysis of complete mitochondrial DNA coding-region sequences for the major African, Asian, and European haplogroups", The American Journal of Human Genetics 70.5 (2002): 1152-1171.
Hogan et al., "Manipulating the mouse embryo", Cold Spring Harbor Press, Cold Spring Harbor, NY, pp. 209-216 and 237-250, 1994.
Holland et al., "Atherogenic levels of low-density lipoprotein increase hydrogen peroxide generation in cultured human endothelial cells: Possible mechanism of heightened endocytosis", Journal of cellular physiology 166.1 (1996): 144-151.
Holt et al., "Deletions of muscle mitochondrial DNA in patients with mitochondrial myopathies", Nature, 331: 717-719, 1988.
Holvoet et al., "Malondialdehyde-modified low density lipoproteins in patients with atherosclerotic disease", Journal of Clinical Investigation 95.6 (1995): 2611-2619.
Hua et al., "Development of bovine-ovine interspecies cloned embryos and mitochondria segregation in blastomeres during preimplantation", Anim. Reprod. Sci. 105:245-57 (2008).
Hunter et al., "Predisposition to Efficient Mammary Tumor Metastatic Progression is Linked to the Breast Cancer Metastasis Suppressor Gene Brms1", Cancer Res., 2001, vol. 61, pp. 8866-8872.
Irwin et al., "Isolation and microinjection of somatic cell-derived mitochondria and germline heteroplasmy in transmitochondrial mice", Transgenic Res. 8:119-23 (1999).
Ischiropoulos, "Biological tyrosine nitration: A pathophysiological function of nitric oxide and reactive oxygen species", Arch. Biochem. Biophys. 356:1-11 (1998).
Ishida et al., "Effects of atherogenic diet consumption on lipoproteins in mouse strains C57BL/6 and C3H", J. Lipid Res. 32:559-68 (1991).
Iuliano et al., "The oxidant stress hypothesis of atherogenesis", Lipids 36:S41-S44 (2001).
Johnson et al., "A nuclear-mitochondrial DNA interaction affecting hearing impairment in mice", Nat. Genet. 27:191-194 (2001).
Kaku et al., "Genetic analysis of glucose tolerance in inbred mouse strains", Diabetes 37:707-13 (1988).
Keefer et al., "Bovine inner cell mass cells as donor nuclei in the production of nuclear transfer embryos and calves", Biol. Reprod. 50:935-9 (1994).
Keith et al., "Increased oxidative stress in patients with congestive heart failure", J. Am. Coll. Cardiol. 31:1352-6 (1998).
Kissner et al., "Formation and properties of peroxynitrite as studied by laser flash photolysis, high-pressure stopped-flow technique, and pulse radiolysis", Chem. Res. Toxicol. 10:1285-92 (1997).
Knight-Lozano et al., "Cigarette smoke exposure and hypercholesterolemia increase mitochondrial damage in cardiovascular tissues", Circulation 105:849-54 (2002).
Knipe et al., "Fields Virology", Eds. Lippincott Williams & Wilkins, 2007, 2007, p. 1.
Kobayashi et al., "Mitochondrial behavior and localization in reconstituted oocytes derived from germinal vesicle transfer", Hum. Cell. 21:7-11 (2008).

(56) References Cited

OTHER PUBLICATIONS

Kong et al., "Phylogeny of East Asian Mitochondrial DNA Lineages inferred from complete sequences", Am. J. Hum. Genet. 73:671-6 (2003).
Lifsted et al., "identification of inbred mouse strains harboring genetic modifiers of mammary tumor age of onset and metastatic progression", Int. J. Cancer 77:640-4 (1998).
Madamanchi et al., "Oxidative stress and vascular disease", Arterioscler. Thromb. Vasc. Biol. 25:29-38 (2005).
Massaeli et al., "Invovlvement of lipoproteins, free radicals, and calcium in cardiovascular processes", Cardiovasc. Res. 29:597-603 (1995).
McMahon et al., "Mitochochondrial DNA sequence diversity in bipolar affective disorder", Am. J. Psychiatry 157:1058-64 (2000).
Minetti et al., "Peroxynitrite induces long-lived tyrosyl radical(s) in oxyhemoglobin of red blood cells through a reaction involving $CO_2$ and a ferryl species", Biochemistry 38:2078-87 (1999).
Napoli et al., "Maternal hypercholesterolemia during pregnanacy promotes early atherogenesis in LDL receptor deficient mice and alters aortic gene expression determined by microarray", Circulation 105:1360-7 (2002).
Niemi et al., "Mitochondrial DNA polymorphisms associated with longevity in a Finnish population", Hum. Genet. 112:29-33 (2003).
Nilsson et al., "Family burden of cardiovascular mortality: risk implications for offspring in a national register linkage study based upon the Malmo preventive project", J. Int. Med. 255:229-35 (2004).
Ohara et al., "Hypercholesterolemia increases endothelial superoxide anion production", J. Clin. Invest. 91:2546-51 (1993).
Paigen et al., "Atherosclerosis susceptibility differences among progenitors of recombinant inbred strains of mice", Arterioscler. 10:316-23 (1990).
Palanichamy et al., "Phylogeny of mitochondrial DNA macrohaplogroup N in India, based on ccomplete sequencing: Implications for the peopling of South Asia", Am. J. Hum. Genet. 75:966-78 (2004).
Parthasarathy et al., "The role of oxidized LDL in atherogenesis", Prog. Lipid Res. 31:127-43 (1992).
Petros et al., "MtDNA mutations increase tumorigenicity in prostate cancer", Proc. Natl. Acad. Sci. USA 102:719-24 (2005).
Pogozelski et al., "The mitochondrial genome sequence of Mus terricolor: Comparison with Mus musculus domesticus and implications for xenomitochondrial mouse modeling", Gene 418:27-33 (2008).
Polites et al., Transgenic Animal Technology: A Laboratory Handbook. (Pinkert, C.A., ed.) Academic Press, San Diego, CA, pp. 15-68 (1993).
Quintana-Murci et al., "Where West meets East: The complex mtDNA landscape of the Southwest and Central Asian corridor", Am. J. Hum. Genet. 74:827-45 (2004).
Radi et al., "Inhibition of mitochondrial electron transport by peroxynitrite", Arch. Biochem. Biophys. 308:89-95 (1994).
Radi et al., "Peroxynitrite reactions with carbon dioxide-bicarbonate", In Methods in Enzymol, vol. 301, (Academic Press), pp. 353-367 (1999).
Reid et al., "Cytotoxicity of oxidised low density lipoprotein to mouse peritoneal macrophages: an ultrastructural study", J. Pathol. 171:321-8 (1993).
Richards et al., "Phylogeography of mitochondrial DNA in western Europe", Ann. Hum. Genet. 62(3):241-260 (1998).
Rose et al., "Paradoxes in longevity: sequence analysis of mtDNA haplogroup J in centenarians", Eur. J. Hum. Genet. 9:701-7 (2001).
Rouse et al., "In utero environmental tobacco smoke (ETS) exposure alters gene expression in lungs of adult Balb/c mice", Environmental Health Perspectives 115:1757-66 (2007).
Ruiz-Pesini et al., "An enhanced MITOMAP with a global mtDNA mutational phylogeny", Nucleic Acids Res. 35:D823-8 (2007).
Ruiz-Pesini et al., "Effects of purifying and adaptive selection on regional variation in human mtDNA", Science 303:223-6 (2004).

Salas et al., "The making of the African mtDNA landscape", Am. J. Hum. Genet. 71:1082-111 (2002).
Sato et al., "Gene therapy for progeny of mito-mice carrying pathogenic mtDNA by nuclear transplantation", Proc. Natl. Acad. Sci. USA 102:16765-70 (2005).
Schildkraut et al., "Coronary risk associated with age and sex of parental heart disease in the Framingham study", Am. J. Cardiology 10:555-9 (1989).
Schurr et al., "Mitochondrial DNA variation in Koryaks and Itel'men: Population replacement in the Okhotsk Sea Bering Sea region during the Neolithic", Amer. J. Phys. Anthropol. 108:1-39 (1999).
Sesso et al., "Maternal and paternal history of myocardial infarction and risk of cardiovascular disease in mean and women", Circulation 104:393-8 (2001).
Sharpe et al., "Interaction of peroxynitrite with mitochondrial cytochrome oxidase", J. Biol. Chem. 273:30961-72 (1998).
Shoffner et al., "MERRF is associated with a mitochondrial DNA tRNALys mutation", Cell 61:931-7 (1990).
Sims et al., "Production of calves by transfer of nuclei from cultured inner cell mass cells", Proc. Natl. Acad. Sci. USA 91:6143-7 (1994).
Sligh et al., "Maternal Germ-Line Transmission of Mutant mtDNAs from Embryonic Stem Cell-Derived Chimeric Mice", PNAS, vol. 97, 2000, pp. 14461-14466.
Steinberg et al., "Beyond cholesterol. Modifications of low-density lipoprotein that increase its atherogenicity", N. Eng. J. Med. 321:1196-7 (1989).
Stephens et al., "The molecular genetics of cardiovascular disease: clinical implications", J. Internal. Med. 253:120-7 (2003).
Sundquist et al., "Differences in maternal and paternal transmission of coronary heart disease", Am. J. Prey. Med. 30:480-6 (2006).
Tabibiazar et al., "Mouse strain specific differences in vascular wall gene expression and their relationship to vascular disease", Arterioscler. Thromb. Vasc. Biol. 25:302-8 (2005).
Tabibiazar et al., "Signature patterns of gene expression in mouse atherosclerosis and their correlation to human coronary disease", Physiol. Genomics 22:213-26 (2005).
Takeda et al., "Characterization of a Donor Mitochondrial DNA Transmission Bottleneck in Nuclear Transfer Derived Cow Lineages", Molecular Reproduction and Development, vol. 75, 2008, pp. 759-765.
Tanaka et al., "Mitochondrial genome variation in eastern Asia and the peopling of Japan", Genome Res. 14:1832-50 (2004).
Tao et al., "Ultrastructural changes in goat interspecies and intraspecies reconstructed early embryos", Zygote 16:93-110 (2008).
Torroni et al., "Harvesting the fruit of the human mtDNA tree", Trends Genet. 22:339-45 (2006).
Trounce et al., "Cybrid models of mtDNA disease and transmission, from cells to mice", Curr. Top. Dev. Biol. 77:157-83 (2007).
Turrens et al., "Generation of superoxide anion by the NADH dehydrogenase of bovine heart mitochondria", Biochem. J. 191:421-7 (1980).
Van Der Walt et al., "Analysis of European mitochondrial haplogroups with AD risk", Neuro. Sci. Lett. 365:28-32 (2004).
Van Der Walt et al., "Mitochondrial polymorphisms significantly reduce the risk of PD", Am. J. Hum. Genet. 72:804-11 (2003).
Wada et al., "Association between parental histories of hypertension, diabetes and dyslipidemia and the clustering of these disorders in offspring", Preven. Med. 42:358-63 (2006).
Wakayama et al., "Full-term development of mice from enucleated oocytes injected with cumulus cell nuclei", Nature 394:369-74 (1998).
Wallace , "A mitochondrial paradigm of metabolic and degenerative diseases, aging, and acner: A dawn for evolutionary medicine", Annu. Rev. Genet. 39:359-407 (2005).
Wallace et al., "Familial mitochondrial encephalomyopathy: genetic, pathophysiological, and biochemical characterization of a mitochondrial DNA disease", Cell 55:601-10 (1988).
Wallace et al., "Mitochondrial DNA mutation associated with Leber's hereditary optic neuropathy", Science 242:1427-30 (1988).
Wallace , "The mitochondrial genome in human adaptive radiaton and disease: on the road to therapeutics and performance enhancement", Gene 354:169-80 (2005).

(56) References Cited

OTHER PUBLICATIONS

Wang et al., "Positional identification of TNFSF4, encoding OX40 ligand, as a gene that influences atherosclerosis susceptibility", Nat. Genet. 37:365-72 (2005).

Witztum et al., "Role of oxidized low density lipoprotein in atherogenesis", J. Clin. Invest. 88:1785-92 (1991).

Wuschke et al., "A meta-analysis of quantitative trait loci associated with body weight and adiposity in mice", Int. J. Obesity. 31:829-41 (2007).

Yakes et al., "Mitochondrial DNA damage is more extensive and persists longer than nuclear DNA damage in human cells following oxidative stress", Proc. Natl. Acad. Sci. USA 94:514-9 (1997).

Yang et al., "Prenatal environmental tobacco smoke exposure promotes adult atherogenesis and mitochondrial damage in apoE −/− mice fed a chow diet", Circulation 110:3715-20 (2004).

* cited by examiner

MITOCHONDRIAL-NUCLEAR EXCHANGED CELLS, TISSUES, ORGANS AND ANIMALS

CROSS-REFERENCE TO RELATED APPLICATION

The present application is a continuation of U.S. Ser. No. 13/360,344, filed Jan. 27, 2012 which is a continuation of U.S. Ser. No. 12/486,375, filed Jun. 17, 2009, which claims priority to U.S. Provisional Application No. 61/076,260, filed Jun. 27, 2008, which are incorporated by reference herein in their entireties.

STATEMENT REGARDING FEDERALLY FUNDED RESEARCH

This invention was made with government support under Grant No. W91XWH-07-1-0540 awarded by the Department of Defense. The government has certain rights in the invention.

BACKGROUND

Each cell contains hundreds of mitochondria and thousands of mitochondrial DNA (mtDNA) copies, which are maternally inherited. The mammalian mtDNA encodes 13 polypeptides that are essential for oxidative phosphorylation (OXPHOS) plus two rRNAs (12S and 16S) and 22 tRNAs that are required for mitochondrial protein synthesis. The mtDNA encoded polypeptide genes are structural subunits for four of the five OXPHOS enzyme complexes (I, III, IV and V). The nuclear DNA (nDNA) codes for all other mitochondrial proteins including all four subunits of complex II (succinate dehydrogenase), the mitochondrial DNA polymerase K subunits, the mitochondrial RNA polymerase components, the mitochondrial transcription factor (mt-TFA), the mitochondrial ribosomal proteins and elongation factors, and the mitochondrial metabolic enzymes. Mitochondria generate energy via OXPHOS which "couples" electron transport with proton translocation for the production of ATP. Mitochondria are also the primary source of endogenous cellular ROS. The efficacy of mitochondrial energy and oxidant production is dependent upon a number of factors including local concentrations of both reactive nitrogen and oxygen species, mitochondrial antioxidants, cytokines, electron transport efficiency, metabolic reducing equivalent availability (NADH and FADH2), uncoupling protein (UCP) activities, and overall organelle integrity (damage to membranes, DNA, and proteins).

SUMMARY

Provided herein are cells and animals comprising mitochondrial DNA (mtDNA) from a subject susceptible to a disease or disorder and nuclear DNA (nDNA) from a subject that is not susceptible to the disease or disorder. Also provided are cells and animals comprising mitochondrial DNA (mtDNA) from a subject resistant to a disease or disorder and nuclear DNA (nDNA) from a wild-type subject or a subject that is susceptible to the disease or disorder. Such animals are referred to herein as mitochondrial-nuclear exchanged animals. Also provided are progeny of mitochondrial-nuclear exchanged animals and progeny animals resulting from a cross between the mitochondrial-nuclear exchanged animals and a knockout mouse, wherein the knockout mouse comprises a mutation in at least one gene associated with the disease or disorder such that the gene is not expressed or the protein expressed by the gene is not functional.

Methods for producing a mitochondrial-nuclear exchanged animal and animals made by the methods are provided. The method comprises selecting an animal susceptible to a disease or disorder, selecting an animal that is not susceptible to the disease or disorder, harvesting pronuclear embryos from the animals, enucleating the embryos, transferring the nucleus from the animal that is not susceptible to the disease or disorder to the enucleated embryo of the animal susceptible to the disease or disorder, wherein the embryo has mtDNA from the animal susceptible to the disease or disorder and the nDNA from the animal that is not susceptible to the disease or disorder, and transferring the embryo into an appropriate host and allowing the transferred embryo to develop into a progeny animal, wherein the progeny animal is a mitochondrial-nuclear exchanged animal.

Also provided is a method of screening for agents useful for treating a disease or disorder comprising the steps of providing a mitochondrial-nuclear exchanged animal comprising mtDNA from an animal susceptible to the disease or disorder and nDNA from an animal not susceptible to the disease or disorder, administering to the animal an agent to be tested, and determining whether the agent prevents or reduces one or more symptoms of the disease or disorder.

The details of one or more aspects are set forth in the accompanying drawings and the description below. Other features, objects, and advantages will be apparent from the description and drawings, and from the claims.

DESCRIPTION OF DRAWINGS

In FIG. 8A, complex IV activity was determined by measuring the oxidation of reduced cytochrome c at 550 nm (37° C.) in isolated mitochondria. Asterisks (*) indicate a significant difference exists between C57 and C3H mitochondria. In FIG. 8B, immunoblot analysis showing the relative level of complex IV subunit II from an aliquot of the samples used for complex IV activity.

DETAILED DESCRIPTION

MtDNA mutations have been linked with human disease. For example, studies have shown that specific mtDNA mutations and haplotypes are associated with increased risk for diseases thought or known to have an environmental component in humans (e.g., deafness, blindness, Alzheimer's disease, diabetes and cancer). Similarly, studies have shown that the mtDNA haplotype can influence tumor growth and age-related deafness in mice. Mitochondrial haplotypes thought to be associated with tightly coupled mitochondria appear to be more prone to certain types of cancer and neurodegenerative diseases associated with oxidative stress and/or somatic mutation. Because it is difficult to examine multiple molecular mechanisms related to many of the aforementioned aspects of mitochondria (e.g., damage, membrane potential, oxidant stress, respiratory activity and enzyme function) in human populations, animal models are required to test the molecular aspects of the mitochondrial-nuclear interaction in determining individual disease susceptibility.

Thus, provided herein are chimeric animals, or cells, tissues or organs thereof with the mitochondrial DNA (mtDNA) from of one cell type (genetic background) and the nuclear DNA (nDNA) from of another cell type, also referred to herein as mitochondrial-nuclear exchanged animals, cells, tissues or organs. Within the cell, mitochondria and the nucleus interact in a manner that ultimately determines how the cell will function and respond to various endogenous and exogenous factors. Consequently, how mitochondria and the nucleus interact determines an individual's susceptibility to disease and the individual's ability to adapt to changes in the environment. Hence, the provided methods allow exchange of mitochondrial and nuclear genetic materials (i.e., putting a cell nucleus into a cytoplasm containing mitochondria that are typically not associated with that nuclear DNA) and model systems for determining how mtDNA impacts disease development and susceptibility to factors associated with disease risk and adaptation to general environmental changes. The provided chimeric models and cells are used to determine the mechanistic and genetic basis of disease susceptibility and resistance (e.g., cardiovascular disease, cancer, diabetes, musculoskeletal, neurological, obesity, aging, fitness, and the like).

Figure 5:
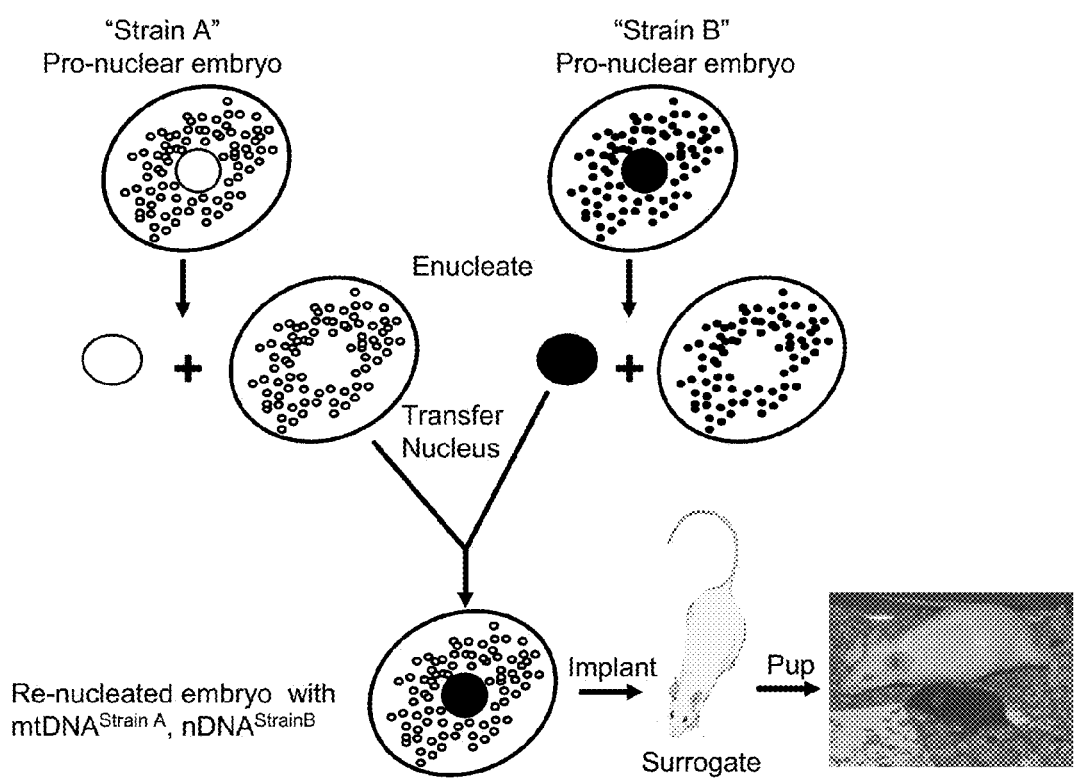
FIG. 5 is a schematic summarizing the process of creating mitochondrial-nuclear exchanged animals.

FIG. 5 summarizes the process of creating mitochondrial-nuclear exchanged animals. Specifically, pro-nuclear embryos are harvested from genetically distinct donors (in terms of mitochondrial and nuclear DNAs), enucleated, and the nucleus from one donor is introduced into the enucleated cell of the other, generating an re-nucleated embryo with the nuclear DNA from one strain (e.g., strain B) and the mitochondrial DNAs (e.g., strain A) from the other. These embryos are implanted into surrogate mothers who carry the transgenic embryo to term. The genetic identity of the progeny is confirmed via genotyping tail and ear clips from the offspring. Females of desired mtDNA-nDNA genotype are then used as founding breeders to establish colonies useful as model systems of mitochondrial-nuclear interaction and disease susceptibility (e.g., females from these colonies are used to establish mitochondrial-nuclear exchanged colonies of any transgenic animal currently available for biomedical research).

Provided are animals, cells, tissues or organs comprising mitochondrial DNA (mtDNA) from a subject susceptible to a disease or disorder and nuclear DNA (nDNA) from a subject that is not susceptible to the disease or disorder. Optionally, the nDNA is from a wild-type subject. Optionally, the nDNA is from a subject resistant to the disease or disorder.

As used herein, a subject susceptible to a disease or disorder refers to a subject having or at risk for developing one or more symptoms associated with the disease or disorder. Thus, subjects susceptible to the disease or disorder have an increased rate of occurrence or a faster onset of one or more symptoms of the disease or disorder as compared to a wild-type subject. Subjects susceptible to the disease or disorder may have a family history or known genetic predisposition for developing the disease or disorder. As used herein, wild-type subjects refer to subjects without the disease or disorder and without enhanced resistance or susceptibility to a disease or disorder of interest. As used herein, a subject resistant to the disease or disorder refers to a subject less likely to develop the disease or disorder than a wild-type subject. Thus, subjects resistant to the disease or disorder have a decreased rate of occurrence or a lower onset of the disease or disorder as compared to a wild-type subject. Subjects resistant to the disease or disorder can include partial or total resistance as compared to wild-type subject. Further a subject can be referred to as wild-type in the context of one disease or disorder while referred to as susceptible in the context of another disease or disorder. For example, a subject can be referred to as wild-type in the context of cancer, but referred to as susceptible in the context of cardiovascular disease. In other words, the subject is not prone to cancer but is prone to cardiovascular disease.

Also provided are animals, cells, tissues or organs comprising mitochondrial DNA (mtDNA) from a subject resistant to a disease or disorder and nuclear DNA (nDNA) from a wild-type subject or a subject that is susceptible to the disease or disorder.

The disease or disorder is, for example, cancer, cardiovascular disease, diabetes, neurological disorder, aging, metabolic disorder, immune disorder, obesity, and musculoskeletal disorder. Optionally, the cell is an oocyte or an embryonic cell. Also provided are zygotes and embryos, such as pro-nuclear embryos comprising the cells.

Optionally, the cells are obtained from any animal including, mammals, birds and amphibians. Suitable mammalian sources include sheep, bovines, ovines, pigs, horses, rabbits, guinea pigs, mice, hamsters, rats, primates, and the like. Optionally, the pro-nuclear embryos are obtained from mice. Optionally, the cells are not human cells.

Other human and animal cells useful in the present disclosure include, by way of example, epithelial, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells. Moreover, the human cells used for nuclear exchange may be obtained from different organs, e.g., skin, lung, pancreas, liver, stomach, intestine, heart, reproductive organs, bladder, kidney, urethra and other urinary organs, and the like. These are just examples of suitable donor and recipient cells. Suitable donor and recipient cells may be obtained from any cell or organ of the body. This includes all somatic or germ cells.

Methods of screening for agents useful for treating a disease or disorder are provided. Such a screening method comprises the steps of providing a mitochondrial-nuclear exchanged cell, tissue or organ, contacting the cell, tissue or organ with a candidate agent to be tested and determining whether the agent prevents or reduces one or more symptoms of the disease or disorder. Optionally, the cells, tissues or organs are obtained from a mitochondrial-nuclear exchanged animal. Suitable tissues and organs include, skin, lung, muscle, cartilage, bone, bone marrow, pancreas, liver, stomach, intestine, heart, reproductive organs, bladder, kidney, urinary organs, and the like.

By way of example, cardiovascular disease is associated with increased levels of oxidants, and an agent useful in treating cardiovascular disease causes decreased levels of oxidants. Thus, the determining step is, optionally, determining the level of oxidants in the cells. Alternatively, the determining step includes assessing mitochondrial function in the cells to determine whether the agent is useful in treating the disease or disorder. Such methods are known and are described in the Examples below. By way of another example, cancer is associated with increased cellular proliferation as compared to wild-type cells. Thus, the determining step is, optionally, determining the rate of proliferation of the cells.

Such methods allow one skilled in the art to select candidate agents that are useful in treating, reducing or preventing one or more symptoms of the disease or disorder. Such agents may be useful as active ingredients included in pharmaceutical compositions for treating a subject suffering from the disease or disorder.

Also provided are chimeric animals comprising a plurality of the provided cells. Such chimeric animals are also referred to herein as mitochondrial-nuclear exchanged animals. Thus, provided herein are chimeric animals comprising mitochondrial DNA (mtDNA) from a subject susceptible to a disease or disorder and nuclear DNA (nDNA) from a subject that is not susceptible to the disease or disorder. Also provided herein are chimeric animals comprising mtDNA from a subject resistant to a disease or disorder and nDNA from a wild-type subject or a subject that is susceptible to the disease or disorder. By way of example, the animal is a mouse comprising mtDNA from C57BL/6J mice and nDNA from C3H/HeN mice. Optionally, the animal is a mouse comprising mtDNA from C3H/HeN mice and nDNA from C57BL/6J mice. By way of another example, the animal is a mouse comprising mtDNA from NZB/B1NJ mice, C57BL/6J mice or AKR/J mice and nDNA from FVB/N-TgN(MMTVPyMT) mice. By way of another example, the animal is a mouse comprising mtDNA from NZB/B1NJ mice and nDNA from C57BL/6J mice. Optionally, the animal is a mouse comprising mtDNA from C57BL/6J mice and nDNA from NZB/B1NJ mice.

As used herein, the term chimeric animal refers to non-human animals, including, mammals, amphibians and birds. Specifically, examples include sheep, feline, bovines, ovines, pigs, horses, rabbits, guinea pigs, mice, hamsters, rats, primates, and the like. Optionally, the animal further comprises a mutation in a gene associated with the disease or disorder. Optionally, the gene is not expressed or the protein expressed by the gene is non-functional. For example, the animal optionally comprises a mutation in SOD2 or ApoE such that SOD2 or ApoE is not expressed or the protein expressed by the gene is non-functional.

Also provided are progeny of the chimeric animals and progeny animals resulting from a cross between the female chimeric animal and a knockout mouse, wherein the knockout mouse comprises a mutation in at least one gene associated with the disease or disorder such that the gene is not expressed or the protein expressed by the gene is not functional. Optionally, the knockout mouse is susceptible to the disease or disorder or resistant to the disease or disorder.

Also provided are methods for producing a mitochondrial-nuclear exchanged animal and a mitochondrial-nuclear exchanged animal made by the provided method. The method comprises selecting an animal susceptible to a disease or disorder or an animal resistant to the disease or disorder; selecting an animal that is not susceptible to the disease or disorder or an animal that is not resistant to the disease or disorder; harvesting the pro-nuclear embryos from each of the animals; enucleating the embryos; transferring the nucleus from the embryo of the animal that is not susceptible to the disease or disorder to the enucleated embryo of the animal susceptible to the disease or disorder to make a resulting embryo, wherein the resulting embryo has mtDNA from the animal susceptible to the disease or disorder and the nDNA from the animal that is not susceptible to the disease or disorder; and transferring the resulting embryo into an appropriate host. The transferred embryo is then allowed to develop into a progeny animal. The progeny animal is a mitochondrial-nuclear exchanged animal. Optionally, the animal that is not susceptible to the disease or disorder is from a wild-type animal or an animal resistant to the disease or disorder. Optionally, the method further comprises selecting female mitochondrial-nuclear exchanged animals for further breeding.

A method of generating progeny of the female mitochondrial-nuclear exchanged animals is provided by crossing the females with a knockout animal, wherein the knockout animal comprises a mutation in at least one gene associated with the disease or disorder such that the gene is not expressed or the protein expressed by the gene is not functional. Optionally, the method further comprises selecting progeny animals of the cross that comprise mtDNA from the mitochondrial-nuclear exchanged animals and nDNA from the knockout mouse.

In the provided methods, the disease or disorder of interest is, optionally, cancer, cardiovascular disease, diabetes, neurological disorder, aging, metabolic disorder, immune disorder, obesity, or musculoskeletal disorder. Other disease and disorders are contemplated and can be of interest when animals with reduced resistance or enhanced susceptibility are accessible.

Methods of nuclear exchange are known and include the methods described in the examples below and those described in, for example, U.S. Publication No. 2003/0032180; U.S. Publication No. 2005/0120402; U.S. Publication No. 2005/0095704; and U.S. Pat. No. 6,603,059, which are incorporated by reference herein in their entireties. Nuclear exchange is also described in U.S. Pat. Nos. 4,944,384; 5,057,420; Campbell et al., Theriogenology, 43:181 (1995); Collas et al., Mol. Report Dev., 38:264-267 (1994); Keefer et al., Biol. Reprod., 50:935-939 (1994); Sims et al., Proc. Natl. Acad. Sci., USA, 90:6143-6147 (1993); WO 94/26884; WO 94/24274, and WO 90/03432, which are incorporated by reference in their entireties herein.

Animals known to be susceptible or resistant to specific diseases are obtained, for example, from the Jackson Laboratory or other commercial or non-commercial sources. By way of example, mice used in the provided methods include, but are not limited to, C57BL/6J, C3H/HeN, AKR/J, FVB strains, BALB/c strains, A/J strains, 129 strains and DBA/2 strains. Wild-type animal models can also be obtained from commercial and non-commercial sources. Mouse models known to be susceptible to specific diseases are listed in the Mouse Phenome Database at http://phenome.jax.org/pub-cgi/phenome/mpdcgi?rtn=docs/home, which is incorporated herein by reference in its entirety. For example, 29 strains are listed in the Mouse Phenome Database as being susceptible to cancer. By way of another example, over 50 strains are listed in the Mouse Phenome Database as being susceptible to cardiovascular disease. A few mouse models are discussed in detail below; however, any subject susceptible, resistant or wild-type can be used in the provided methods to generate mitochondrial-nuclear exchanged animals.

Mice useful in the provided methods include, A/J mice, which are susceptible to cancers and resistant to cardiovascular disease. A/J mice have a high incidence of spontaneous lung adenomas, lung tumors that readily develop in response to carcinogens, and mammary adenocarcinomas. A/J mice fed an atherogenic diet (1.25% cholesterol, 0.5% cholic acid, and 15% fat) fail to develop atherosclerotic aortic lesions in contrast to several highly susceptible strains of mice. In addition to atherosclerosis resistance, A/J mice are resistant to diabetes, obesity, insulin resistance and glucose intolerance.

FVB/N-TgN(MMTV-PyMT) mice carrying the (MMTV-PyVT) transgene are susceptible to cancer.

C57BL/6 mice are commonly used as a general purpose strain and background strain. This strain is refractory to many tumors. C57BL/6J mice are also commonly used in the production of transgenic mice. This strain can be used as a wild-type strain in many contexts. However, the C57BL/6J strain can be used in the context of cardiovascular disease as a susceptible animal since C57BL/6J mice are highly susceptibility to diet-induced obesity, type 2 diabetes, and atherosclerosis. Thus, C57BL/6J mice can be considered a subject susceptible to obesity, diabetes or cardiovascular disease or as a wild-type subject in the study of other diseases such as immunological diseases or cancer.

NZB/B1NJ mice display a number of autoimmune abnormalities including hemolytic anemia, elevated levels of immunoglobulin, anti-DNA antibodies, anti-thymocyte antibodies, and circulating immune complexes causing glomerulonephritis. F1 hybrids of NZB/B1NJ and NZW/LacJ (NZBWF1/J) are used as a model for autoimmune disease resembling human systemic lupus erythematosus. NZB/B1NJ mice, fed an atherogenic diet (1.25% cholesterol, 0.5% cholic acid and 15% fat), fail to develop atherosclerotic aortic lesions. NZB/B1NJ mice can be used as animals susceptible to autoimmune disorders or as animals resistant to cardiovascular disease. By way of example, mice known to be susceptible (NZB/B1NJ) to automimmune disorders will be used in nuclear exchange experiments to generate mice with a NZB/B1NJ mtDNA haplotype and a nuclear genome of a normal mouse or a mouse resistant to autoimmune disorders. These mice are generated using the method set forth in Example 1 below.

AKR/J mice are widely used in cancer research for their high leukemia incidence. AKR/J mice, however, are relatively resistant to aortic lesion formation on a semi-synthetic high fat diet and are hyporesponsive to diets containing high levels of fat and cholesterol. Thus, AKR/J mice are referred to as resistant to cardiovascular disease, but susceptible to cancer, and can be used accordingly in the present methods and cells.

DBA/2J is a widely used strain in a large number of research areas, including cardiovascular biology, neurobiology, and sensorineural research. DBA/2J mice show a low susceptibility to developing atherosclerotic aortic lesions (20 to 350 Tm2 atherosclerotic aortic lesions/aortic cross-section) following 14 weeks on an atherogenic diet (1.25% cholesterol, 0.5% cholic acid and 15% fat). They also exhibit high-frequency hearing loss beginning roughly at the time of weaning/adolescence (between 3-4 weeks of age) and becoming severe by 2-3 months of age. DBA/2J mice also show an extreme intolerance to alcohol and morphine. Thus, DBA/2J mice can be used as susceptible to neurologic disorders and hearing loss, but resistant to cardiovascular disease and substance abuse or addiction.

Methods of screening for agents useful for treating a disease or disorder are provided comprising the steps of providing a mitochondrial-nuclear exchanged animal comprising mtDNA from an animal susceptible to the disease or disorder and nDNA from an animal not susceptible to the disease or disorder, administering to the animal an agent to be tested, and determining whether the agent prevents or reduces one or more symptoms of the disease or disorder. Optionally, the animal not susceptible to the disease or disorder is a wild-type animal or an animal resistant to the disease or disorder. Optionally, the disease or disorder is selected from the group consisting of cancer, cardiovascular disease, diabetes, neurological disorder, aging, metabolic disorder, immune disorder, obesity, and musculoskeletal disorder. Optionally, the disease is cancer and the mitochondrial-nuclear exchanged animal is a mouse comprising mtDNA from a mouse selected from the group consisting of FVB/N-TgN(MMTVPyMT), AKR/J, and A/J mice. Optionally, the disease is cardiovascular disease and the mitochondrial-nuclear exchanged animal is a mouse comprising mtDNA from C57BL/6J or DBA/2J mice. Optionally, the mitochondrial-nuclear exchanged animal is a mouse comprising mtDNA from C57BL/6J mice and nDNA from C3H/HeN mice. Optionally, the mitochondrial-nuclear exchanged animal is a mouse comprising nDNA from a mouse selected from the group consisting of C57BL/6J, 129, A/J, BALB/c and C3H/HeN mice.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation may not be explicitly disclosed, each is specifically contemplated and described herein. For example, if a chimeric animal is disclosed and discussed and a number of modifications that can be made to the chimeric animal are discussed, each and every combination and permutation of the chimeric animal, and the modifications that are possible are specifically contemplated unless specifically indicated to the contrary. Likewise, any subset or combination of these is also specifically contemplated and disclosed. This concept applies to all aspects of this disclosure including, but not limited to, steps in methods of using the disclosed compositions or animals. Thus, if there are a variety of additional steps that can be performed it is understood that each of these additional steps can be performed with any specific method steps or combination of method steps of the disclosed methods, and that each such combination or subset of combinations is specifically contemplated and should be considered disclosed.

Throughout this application, various publications are referenced. The disclosures of these publications in their entireties are hereby incorporated by reference into this application.

A number of aspects have been described. Nevertheless, it will be understood that various modifications may be made. Furthermore, when one characteristic or step is described it can be combined with any other characteristic or step herein even if the combination is not explicitly stated. Accordingly, other aspects are within the scope of the claims.

EXAMPLES

Example 1

Mitochondrial Influence on Breast Cancer Metastasis Susceptibility

It is widely appreciated that carcinogenic risk may be influenced by a combination of genetic and environmental factors that influence an individual's predilection to metastatic tumor formation. In this respect, numerous studies have investigated and reported that nuclear genetic differences may influence susceptibility to breast cancer; other reports suggest a potential role for the mitochondrion in influencing tumor metastatic potential. In this regard, an important consideration currently lacking in determining individual susceptibility to breast cancer metastasis is the potential role for mitochondrial-nuclear interaction.

Mitochondria have been implicated to play a significant role in the etiology of a variety of diseases, including cancer. Certain human mitochondrial DNA haplotypes appear to increase the risk for certain types of cancer and tumor growth in mice. Genetic background also influences metastatic mammary tumor formation in mice. To test whether mitochondrial-nuclear exchanged interaction influences metastatic susceptability, a molecular genetic approach was developed to investigate the role of mitochondrial genetic background on breast cancer metastasis. Specifically, mice known to be resistant (C57BL/6JNlcr) to metastasis in a metastatic mammary tumor model (FVB/N-TgN(MMT-VPyMT transgenic mouse) were used in nuclear exchange experiments to generate mice with a C57BL/6J mtDNA haplotype and FVB/N-TgN nuclear genome and vice versa.

Specifically, fertilized oocytes were collected from C57BL/6JNlcr, and FVB/N-TgN(MMTVPyMT superovulated donor females. Enucleation of metaphase II oocytes and donor cell nuclear injections were conducted. Briefly, PMSG and hCG were administered to 4-6 wk old donor females, placed with stud males, and oocytes collected at 0.5 days post coitum (dpc). After cumulus cell removal, oocytes (15-20) were placed in a micromanipulation chamber containing M2 medium supplemented with cytoskeletal inhibitors cytochalasin B(5 ug/mL) and Colcemid (0.1 ug/mL) for 5-10 minutes. Using a holding pipette to immobilize an oocyte, the zona pellucida is then "cored" using a single low duration high-intensity piezo-pulse (Primetech piezoelectric drill) from a ground 45 degree-angle enucleation pipette, both pronuclei were carefully aspirated and expelled. When all oocytes had been enucleated, donor oocytes (those providing new nuclear material) were placed in the micromanipulation chamber, and pronuclei were again aspirated and immediately injected into the previously enucleated (recipient) oocytes. Reconstructed nuclear transfer embryos were then rinsed in fresh M2 media and electrofused in 25 uL droplets under oil. Reconstructed nuclear transfer embryos were immediately implanted into the oviducts of 0.5 dpc pseudopregnant females or cultured overnight to the 2-cell stage and then transferred. Surrogate mothers underwent C-sections if pups were not born naturally on their due date and fostered to ICR foster mothers.

Figure 1:
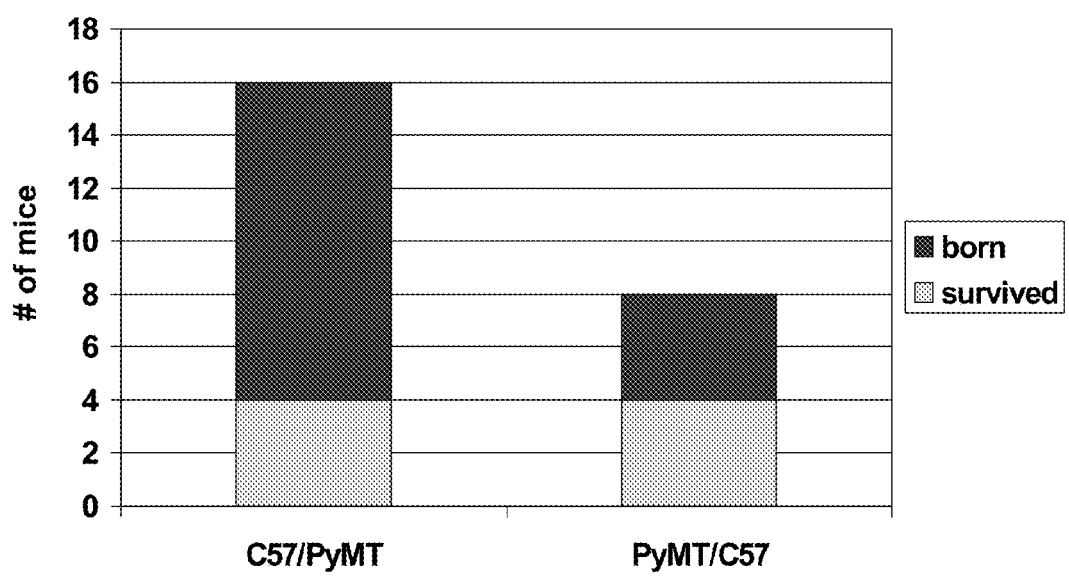
FIG. 1 shows the number of mitochondrial-nuclear exchanges performed resulting in term births, and surviving animals (6 weeks of age). Labels on the X-axis indicate mtDNA haplotype/nuclear genotype. PyMT refers to the FVB/N-TgN(MMTVPyMT) mouse. C57 refers to the C57BL/6JNlcr mouse.

FIG. 1 shows the number of mitochondrial-nuclear exchanges performed resulting in term births, and surviving animals (6 weeks of age). Labels on the X-axis indicate mtDNA haplotype/nuclear genotype. PyMT refers to the FVB/N-TgN(MMTVPyMT) mouse. C57 refers to the C57BL/6JNlcr mouse.

Figure 2A:
FIG. 2A shows a female mitochondrial-nuclear exchanged mouse [C57 mtDNA/FVB/N-TgN(MMT-VPyMT) nuclear DNA (nDNA)] at 3 months of age.
Figure 2B:
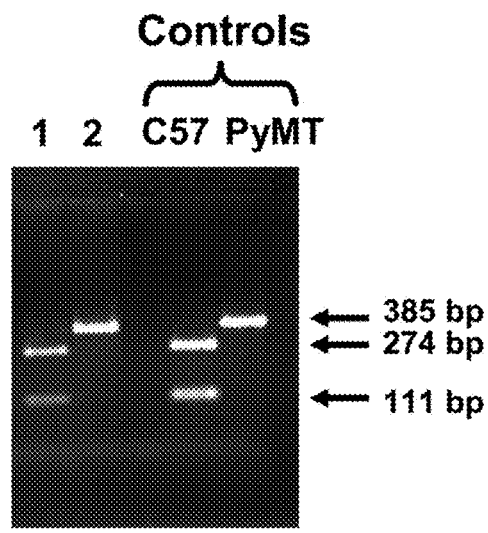
FIGS. 2B and 2C show mtDNA haplotyping gels (Asp I and Bcl I, respectively) to confirm mtDNA haplotype from ear clip DNA; lane 1 is the mouse in FIG. 2A.
Figure 2C:
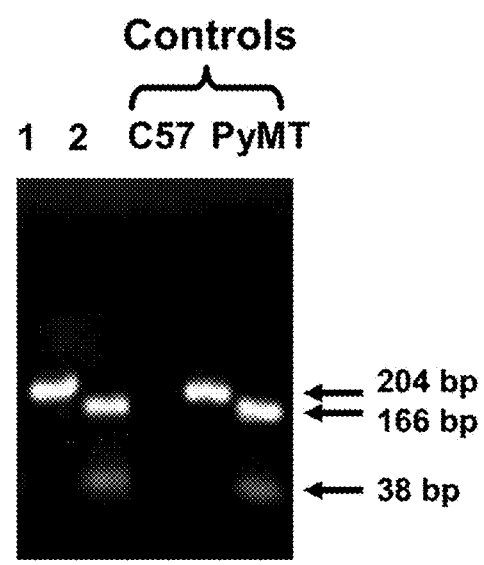

FIG. 2A shows a female mitochondrial-nuclear exchanged mouse [C57 mtDNA/FVB/N-TgN(MMT-VPyMT) nuclear DNA (nDNA)] at 3 months of age. FIGS. 2B and 2C show mtDNA haplotyping gels (Asp I and Bcl I, respectively) to confirm mtDNA haplotype from ear clip DNA; lane 1 is the mouse in panel A.

These data shown mitochondrial-nuclear exchange techniques can be used to successfully generate FVB/N-TgN (MMTVPyMT) transgenic mice on different mtDNA haplotype backgrounds, providing a novel means for direct assessment of mitochondrial-nuclear role(s) on cancer metastasis. As an example of the feasibility of using the mitochondrial-nuclear exchange (MNX) mouse model, one female and three male MNX mice were generated with a C57BL/6J mtDNA and a PyMT nuclear FVB/N genome (mtDNAC57BL/6::nDNAPyMT) (Table 1). Because F1 progeny from PyMT ♂ X C57BL/6 ♀ have a suppressed metastasis index, it was thought that MNX mtDNAC57BL/6::nDNAPyMT mice would have suppressed tumor formation and metastatic potential compared to mice harboring the FVB/N mtDNA (the "wild-type" mtDNA for the PyMT transgenic) and PyMT nuclear genome (mtDNAFVB/N:: nDNAPyMT).

TABLE 1

A summary of the study from the first four mtDNAC57BL/6::nDNAPyMT mice produced.

| Gender | Age | Onset of Primary Breast Tumor | Number of Lung Metastases |
|---|---|---|---|
| MNX Female[a] | 110 days at sacrifice | 79 days | 3 |
| MNX Male[a] | 238 days at sacrifice | 107 days | None detected |
| MNX Male[a] | Currenlty 308 days, not yet sacrificed | None detected | ND |
| MNX Male[a] | Currently 308 days, not yet sacrificed | None detected | ND |
| Female controls[b] | 94 ± 2.35 days at sacrifice | 67.22 ± 3.07 days | 24.63 ± 5.39 |
| Male controls[b,c] | Average age at sacrifice not provided | 83 ± 20 days | Specific number not reported, multiple, 80% penetrance |

ND—not determined
[a]mtDNA$^{C57Bl/6}$::nDNA$^{PyMT}$ mice
[b]mtDNA$^{FVB/N}$::nDNA$^{PyMT}$ mice; Control data are listed as mean + SEM
[c]Male control data are from Hazen and Heinecke, *J. Clin. Invest.* 99:2075-2081 (1997).

"Wild-type" (mtDNA$^{FVB/N}$::nDNA$^{PyMT}$) mice develop mammary tumors and metastases with 100% penetrance within 70 days and ~90 days, respectively. The MNX female mouse (mtDNAC$^{57BL/6}$::nDNA$^{PyMT}$) exhibited slightly longer latency (79 days), but significantly fewer surface lung metastases (3 versus 25 for wild-type mice). Of the three male MNX mice (mtDNAC$^{57BL/6}$::nDNA$^{PyMT}$) generated, only one has developed a mammary tumor (at 107 days), which is substantially longer than "wild-type" PyMT males (mean latency 83 days). When euthanized at 238 days, no metastases were found. The other two males were alive and tumor-free at 320+ days.

These data show that pre-existent normal mitochondrial haplotypes or polymorphisms influence breast cancer latency and metastatic efficiency.

Example 2

Examples of Mitochondrial-Nuclear Exchanged Mice as Cancer Animal Models

Mice known to be susceptible (AKR/J) or resistant (NZB/B1NJ) to metastasis in a metastatic mammary tumor model (FVB/N-TgN(MMTVPyMT transgenic mouse) are used in nuclear exchange experiments to generate mice with a NZB/B1NJ mtDNA haplotype and FVB/N-TgN nuclear genome, and a mouse with a AKR/J mtDNA and FVB/N-TgN nuclear genome. These mice are assessed for metastatic tumor formation compared to mice with FVB mtDNA and FVB/N-TgN nuclear genomes. These mice are generated using the method set forth in Example 1.

Example 3

Mitochondrial-Nuclear Exchanged Mice and Cardiovascular Disease Susceptibility

Figure 3A:
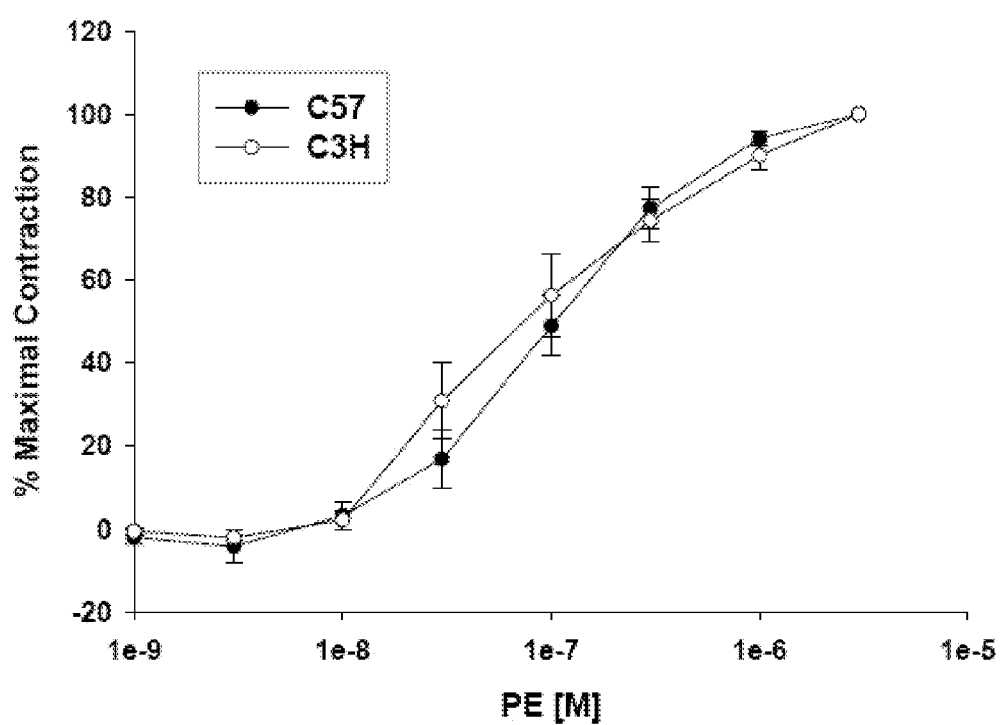
FIGS. 3A, 3B and 3C are graphs showing isometric tension measured in aortic segments from 12-week old male C57 and C3H mice. Thoracic aorta were cut into 2 mm ring segments and suspended from a force-displacement transducer in an isolated tissue bath. To assess endothelium-dependent relaxation, indomethacin-treated rings were contracted with phenylephrine (PE) (FIG. 3A) followed by addition of acetylcholine (Ach) (FIG. 3B). Sodium nitroprusside (SNP) was added to contracted rings to determine endothelial independent relaxation (FIG. 3C). Relaxation was quantified as percent decrease in vessel tension of the pre-existing tone generated by PE. Data are the mean from 3-4 ring segments from each animal (N=4 mice/group). Asterisks (*) indicate significant difference (P<0.05) between the two mouse strains.
Figure 3B:
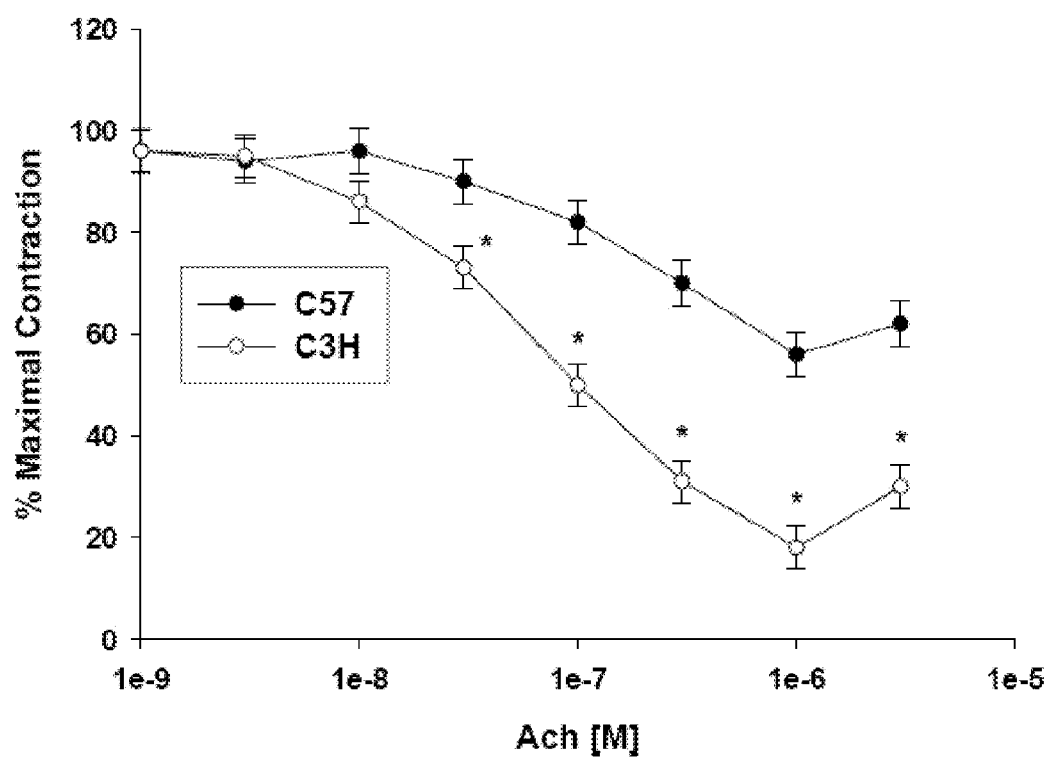
Figure 3C:
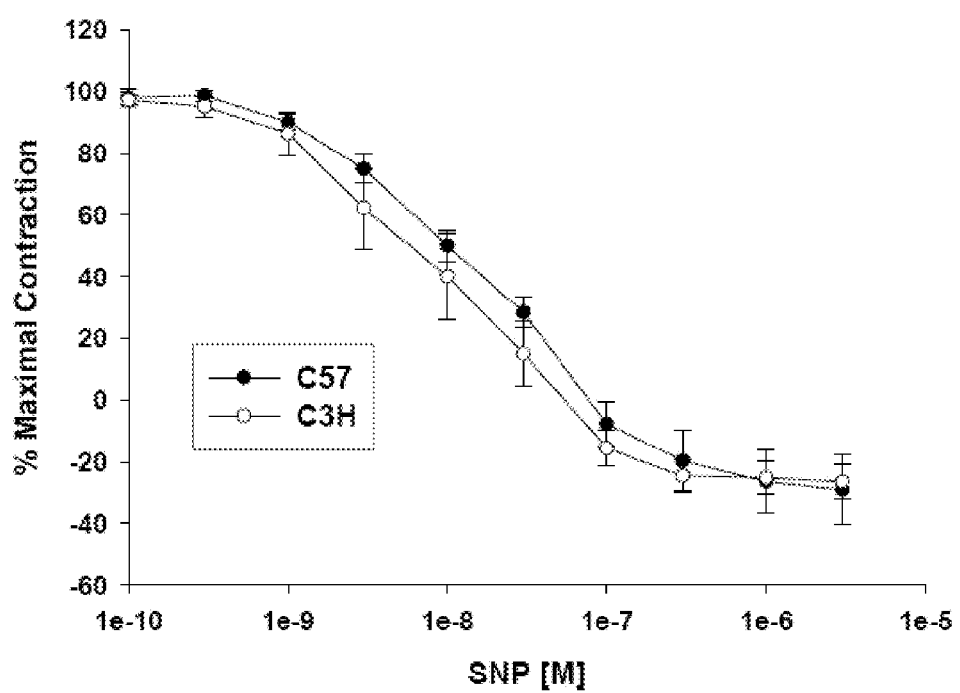

As described herein, mitochondrial-nuclear exchange successfully generated mice with mtDNAs of one strain and the nDNA of another. C57BL/6J mice are prone to cardiovascular disease while C3H/HeN mice are not. C3H mice have increased sensitivity to endothelial dependent vasorelaxation compared to C57 mice. Because C57 mice are more susceptible to atherogenesis compared to C3H mice, it was hypothesized that endothelial dependent vasorelaxation would be decreased in C57 mice relative to C3H mice. Consequently, vessel dilatation studies were performed on C57BL/6 and C3H/HeN mouse aortas harvested from 12 week old mice. FIGS. 3A, 3B and 3C reveal that C3H mice were more sensitive to acetylcholine induced relaxation, whereas no differences were observed in endothelial independent relaxation (SNP), consistent with the hypothesis that C57 mice have decreased endothelial dependent vessel relaxation compared to C3H animals.

Figure 4A:
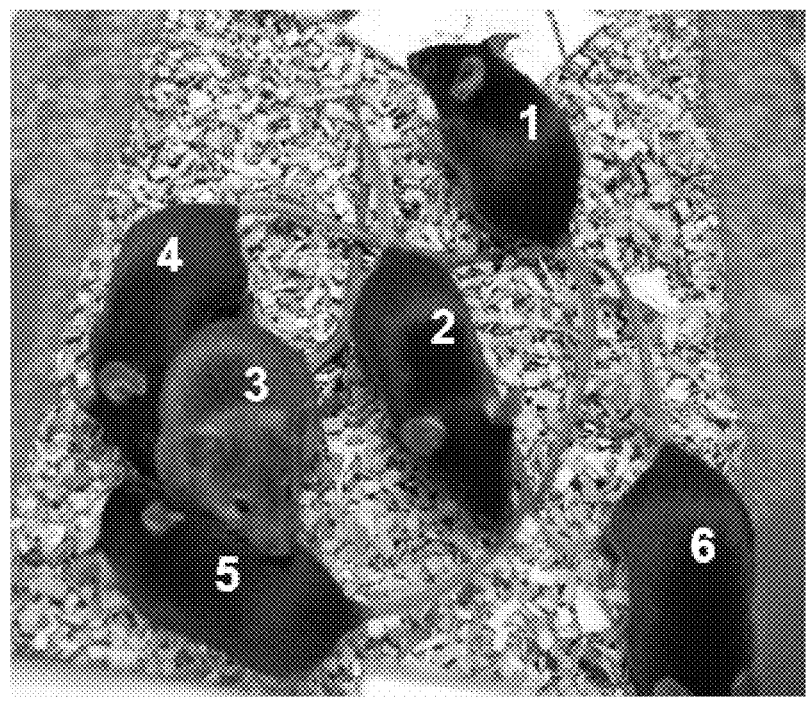
FIG. 4A shows mice generated from mitochondrial-nuclear exchange. Coat color indicates nDNA genome (C3H—brown, C57—black), which has been confirmed via SNP analysis of 38 markers (Jackson Labs, Bar Harbor, Me.). Numbers on mice indicate mtDNA RFLP analyses in FIGS. 4B and 4C. Number 3, brown coat, is the mouse with nDNA from C3H and mtDNA from C57 mice.
Figure 4B:
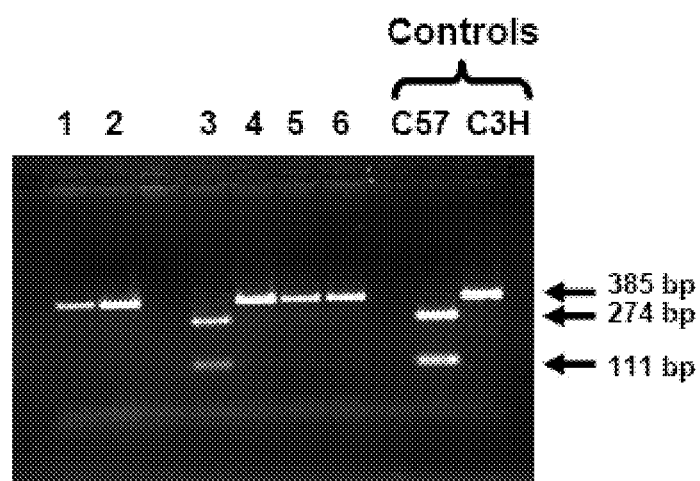
FIG. 4B shows AspI RFLP analysis verifying mtDNA genotype. PCR products from C57 mtDNAs were cleaved by AspI to yield 274 bp and 111 bp fragments, whereas C3H mtDNAs were uncut (385 bp).
Figure 4C:
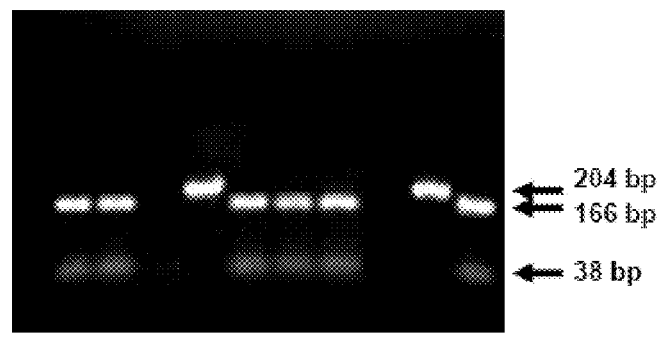
FIG. 4C shows BclI RFLP analysis verifying mtDNA genotype. PCR products from C57 mtDNAs were uncut (204 bp) whereas C3H mtDNAs were cleaved by BclI to yield 166 bp and 38 bp fragments.

To test the hypothesis that the noted differences in mouse strain susceptibility to CVD are related to mtDNA haplotype, mice were generated that have the mtDNA of a susceptible strain (C57) and the nDNA of a resistant strain (C3H) and vice versa. FIG. 4A shows 6 female mice generated by mitochondrial-nuclear exchange using C57 and C3H pronuclear embryos. The 5 mice with black coats have C57 black nuclear DNA, as confirmed by both coat color and typing of 38 strain specific SNPs. These mice also have C3H mouse mitochondrial DNAs (FIGS. 4B and 4C: lanes 1,2 and 4-6), as determined by Asp I and Bcl I RFLP analyses (FIGS. 4B and 4C, respectively). The mouse with brown coat color (#3) has C3H nuclear DNA (confirmed by SNP analysis) and a C57 mtDNA (FIGS. 4B and 4C: Lane 3) by RFLP analysis. These results confirm the feasibility of the proposed mitochondrial-nuclear exchange experiments.

Example 4

Mitochondrial Influence on Cardiovascular Disease Susceptibility

Because it is known that certain mouse strains have differential susceptibilities to CVD development, mitochondrial function and genetics may be important factors in influencing individual CVD susceptibility differences. Such differences in mice known to be susceptible or resistant to CVD were determined. C57BL/6J mice, referred to in Example 4 as C57 mice, are susceptible to dietary induced atherogenesis, whereas C3H/HeN, referred to in Example 4 as C3H mice, are not.

Figure 7:
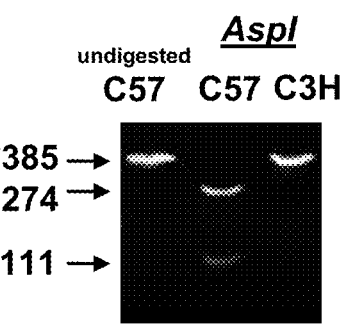
FIG. 7 shows RFLP analysis of mtDNA COIII subunit. Specifically, a gel of AspI restriction digest of 385 bp PCR products from C57 and C3H mice is shown. The C57 mtDNA was cleaved into 274 bp and 111 bp, whereas the C3H mtDNA was not.

Experiments were performed to distinguish between the two mtDNA haplotypes of C57 and C3H. In this respect, C57 and C3H differed at nt 9348 within the COIII gene (G to A, resulting in the change of a highly conserved Val248 to Ile248 in C57 to C3H, respectively). This change abolishes a AspI site in the C3H mtDNA. FIG. 7 shows a 385 bp PCR product from C57 and C3H mice digested with AspI restriction enzyme, indicating that the C57 and C3H mtDNAs are distinguishable. Val248 is conserved between C57 mice, rats, gorillas, humans, frogs and trout.

Figure 8A:
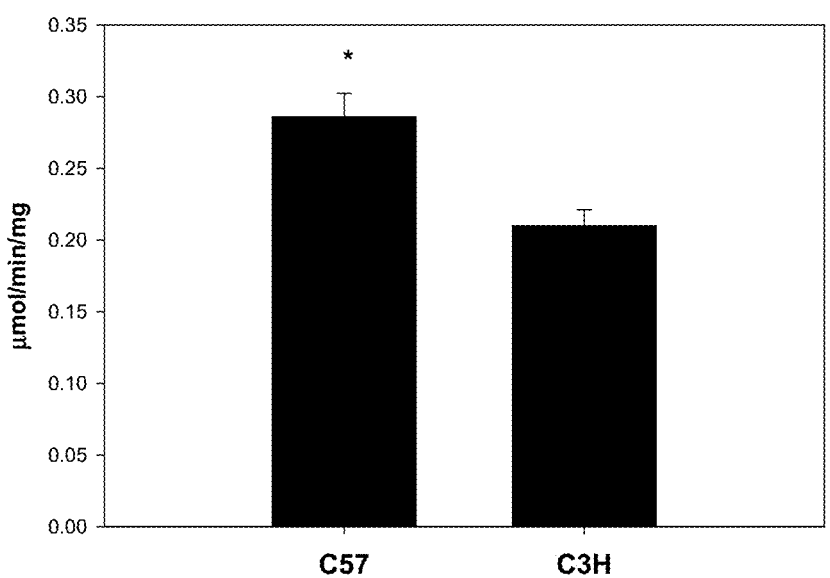
FIGS. 8A and 8B show cytochrome c oxidase activities in C57 and C3H mice. Mitochondria were prepared from whole aortas harvested from 10-week old male C57BL6 and C3H/HeN mice.
Figure 8B:
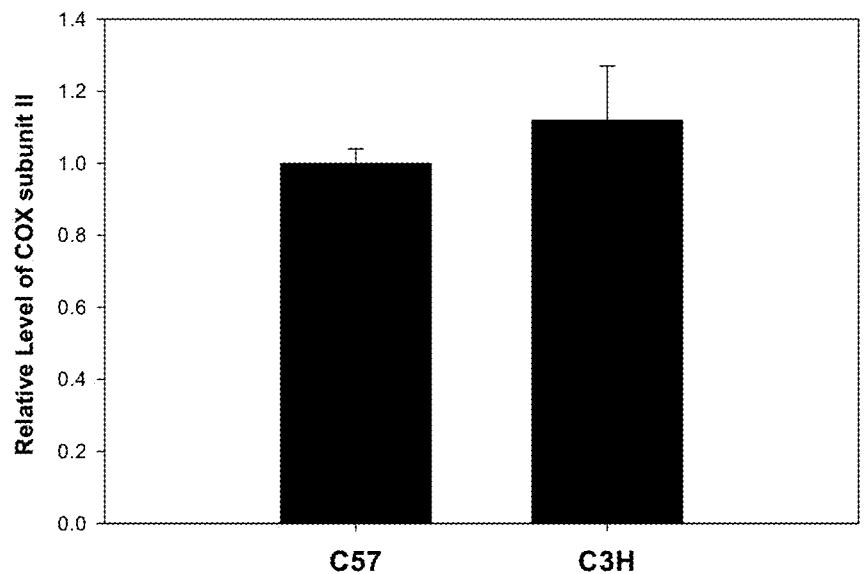

To determine whether the missense mutation in cytochrome oxidase subunit III conveyed any functional effects upon electron transport, mitochondria were isolated from C3H and C57 mice (fed chow diets) and assessed for complex IV activity. FIG. 8A shows that C3H mitochondria had significantly decreased complex IV activity relative to C57 mitochondria. Immunoblot analyses (FIG. 8B) from aliquots used in the enzyme analysis revealed no significant differences in subunit II of complex IV, showing that the observed differences seen in the enzymatic activity were not due to differences in complex IV amounts. These findings were consistent with the concept that there will be functional differences between the atherogenic susceptible C57 and resistant C3H mice.

Figure 9:
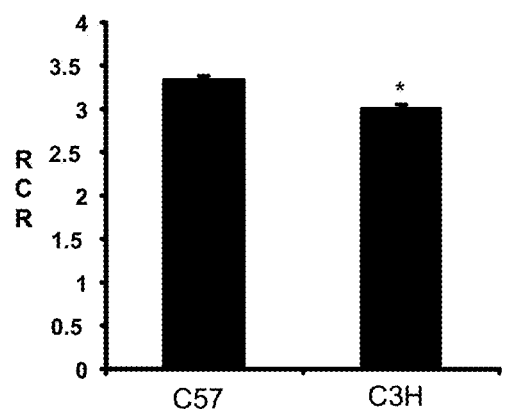
FIG. 9 shows Respiratory Control Ratios (RCR) in C57 and C3H mouse hearts. Mitochondria were isolated from age-matched (10 week old) C57 and C3H mouse hearts, and oxygen consumption determined in the presence of an electron donor (glutamate/malate) with and without ADP (state 3 and 4 respiration, respectively). The bars represent the respiratory control ratio (RCR, equal to state 3 respiration rate divided by state 4 respiration rate); C3H hearts had significantly lower RCR values, indicating that oxygen utilization (in terms of generating ATP) by the mitochondrion is less efficient in the C3H hearts. N=3/group.

To determine whether the mitochondria from C3H mice were different from C57 in terms of oxygen utilization and ATP generation, respiratory control ratios (RCR=state 3/state 4 respiration; oxygen consumption rates in the presence and absence of ADP, respectively) were quantified from mitochondria isolated from heart tissues harvested from male C3H and C57 mice on chow diets. FIG. 9 shows that the RCR in C3H mice appeared decreased relative to the C57 mice, showing that mitochondrial oxidative phosphorylation was less "coupled" to oxygen consumption in the C3H mice, consistent with the hypothesis that C3H have less coupled mitochondria relative to C57 mice, and therefore, are resistant to the oxidant stress associated with CVD risk factors.

Figure 6A:
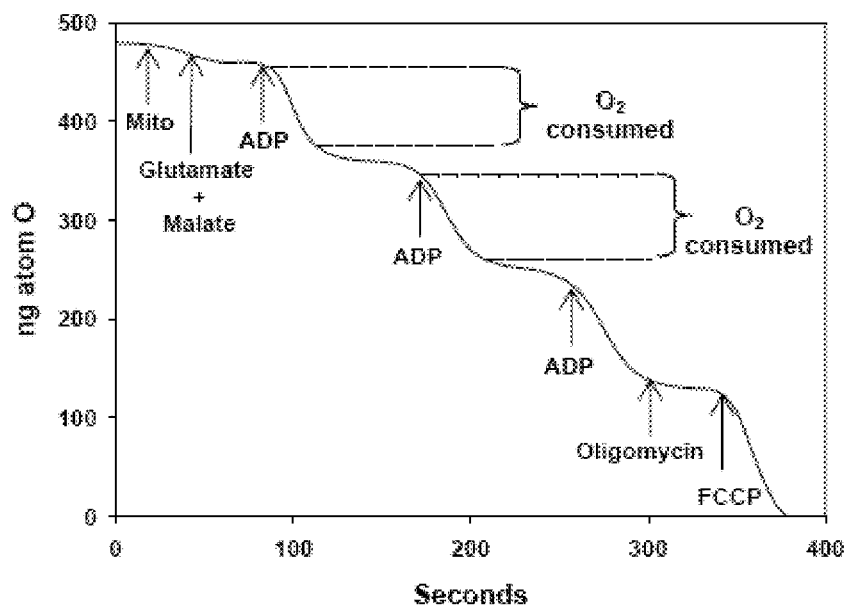
FIG. 6A shows polarographic trace of isolated heart mitochondria. State 3 respiration is initiated by addition substrate (glutamate+malate) and ADP (125 nmoles) and total O2 consumption determined until the return to state 4 respiration (occurs when all the ADP is consumed by phosphorylation to ATP). Addition of oligomycin abolishes ADP-induced respiratory stimulation which is subsequently relieved by the uncoupler carbonyl cyanide p-trifluoromethoxyphenylhydrazone (FCCP).
Figure 6B:
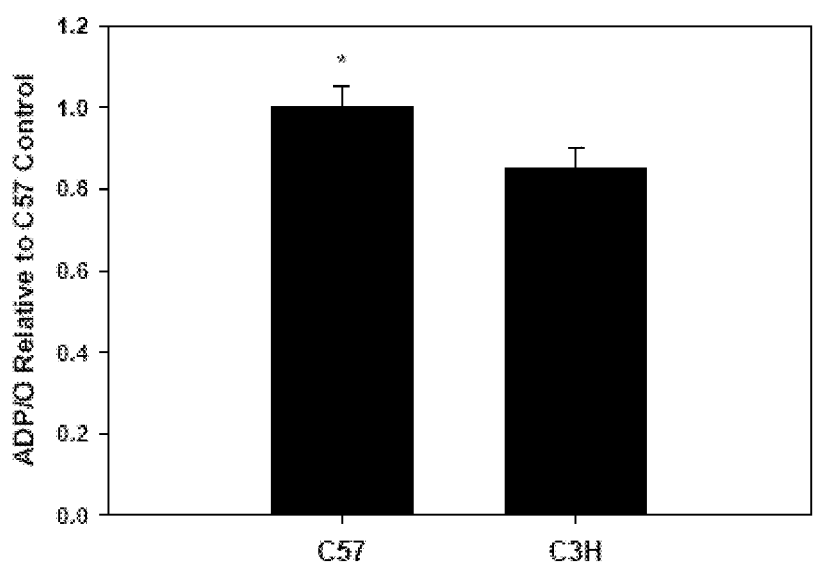
FIG. 6B is a graph showing the ADP/O ratio of C57BL/6J (C57) and C3H/HeN (C3H) mice relative to C57BL/6J control mitochondria. The ADP/O ratio is calculated as the ratio of nanomoles of ADP added, to nanoatoms of oxygen consumed during state 3 respiration. Data are expressed relative to the C57BL/6J control mitochondria because results were obtained from 5 independent experiments, with C57BL/6J mitochondria serving as the control for each separate experiment (N=2 per strain per experiment). The ADP/O mean+SE over all experiments was C57—2.88+0.05; C3H—2.39+0.04). Asterisk (*) indicates a significant difference (P<0.05) exists from C3H/HeN mouse mitochondria.

To evaluate the relative efficiencies of mitochondrial ATP generation coupled to oxygen consumption in C57BL/6J and C3H/HeN mice, 10-C57BL/6J and 10-C3H/HeN mice were harvested at 14 weeks of age over a series of 5 days (N=2 C57BL/6J, and 2-C3H/HeN mice per experiment, per day), and a known amount of ADP (125 nmoles) was added to equal amounts of heart mitochondria isolated from C57 or C3H mice to induce state 3 respiration (malate/glutamate+ADP). The amount of oxygen consumed was quantified to the point of return to state 4 respiration (occurs when all the ADP is consumed by phosphorylation to ATP: FIG. 6A). The ADP/O ratio relative to the C57BL/6J mouse mitochondrial control (determined from 5 independent experiments; 2-C57BL/6J and 2-C3H/HeN mice per experiment), is presented in FIG. 6B, showing that C3H/HeN mice have significantly lower ADP/O ratios compared to C57BL/6J mice. Low ADP/O ratios reflect decreased efficiency of oxygen utilization to make ATP and, thus, less efficient mitochondria. These results showed that C3H/HeN mitochondria consumed more oxygen compared to C57BL/6J mitochondria, per ADP molecule phosphorylated, consistent with the hypothesis that C3H/HeN mice are less energetically efficient compared to C57BL/6J mice.

Figure 10:
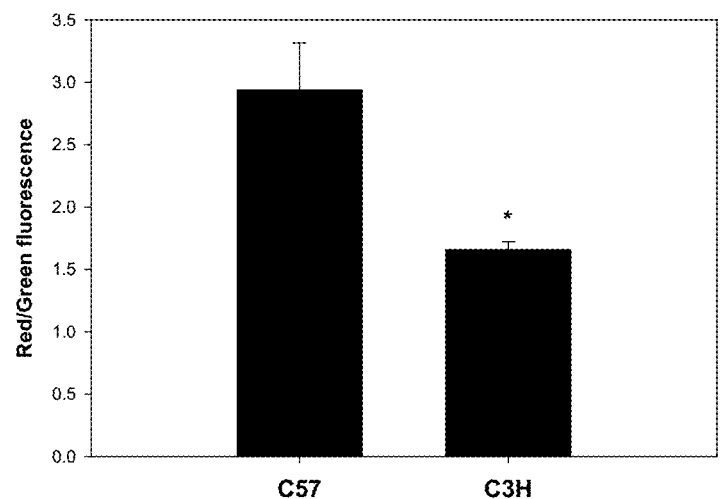
FIG. 10 is a bar graph showing mitochondrial membrane potentials in C57 and C3H mice. Mitochondria were prepared from hearts harvested from 10-week old male C57BL6 and C3H/HeN mice (fed chow diets) and JC-1 fluorescence determined at 535 nm and 590 nm emissions on a CytoFluor 4000 fluorometer. Asterisks (*) indicate that a significant difference exists between C57 and C3H mitochondria.

Because the data above suggested that differences existed between the mitochondria from C3H and C57 mice, JC-1 fluorescence was utilized to determine mitochondrial membrane potentials. JC-1 exists as a green fluorescent monomer at low concentrations or low membrane potential, whereas at higher concentrations (>0.1 Tm) it forms a red-fluorescent "J-aggregate." Consequently, the ratio of red-to-green JC-1 fluorescence is dependent only on the mitochondrial membrane potential and not on other factors that may influence single-component fluorescence signals, such as mitochondrial size, shape and density. FIG. 10 shows that mitochondria isolated from C57 mouse hearts had significantly higher membrane potentials than age matched (10-week old) C3H mitochondria. These findings are consistent with the hypothesis that C3H mice have mitochondria that are less coupled than those of C57 mice.

Figure 11:
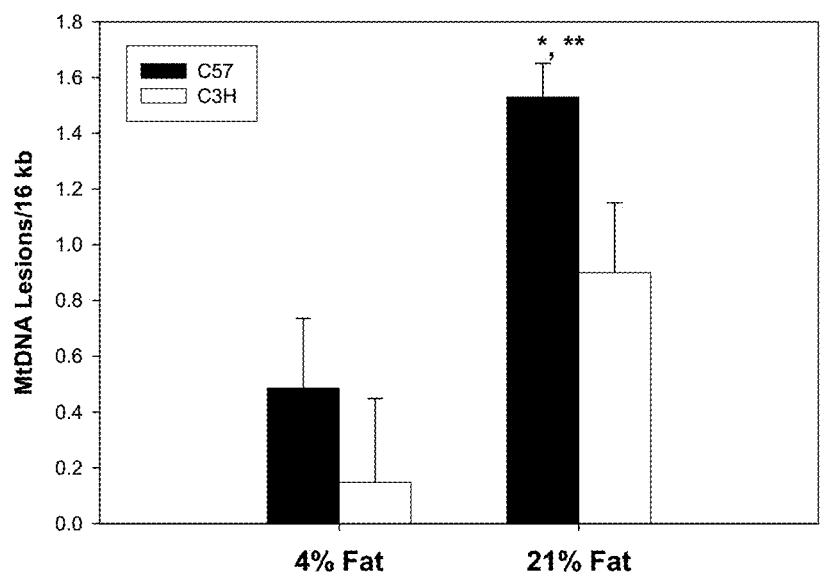
FIG. 11 shows the effect of diet on mtDNA damage in aortas from C57 and C3H mice. Male C57 and C3H mice were fed either chow or high fat diets (4% or 21% fat, respectively) from 6-10 weeks of age. DNA was extracted from aortas and QPCR was performed to quantify mtDNA damage. Asterisks (* or **) indicate significant differences (P<0.05) exist from chow fed C57 or high fat C3H, respectively. N=3 per group.

Because the data above were consistent with the hypothesis that C3H mice were less coupled relative to C57 mice, the impact of a high fat diet on mtDNA damage was assessed in aortic tissues from both C57 and C3H mice. Male C3H and C57 mice were fed either a chow or high fat diet from 6 to 10 weeks of age, and mtDNA damage was determined from aortas. FIG. 11 shows that a high fat diet significantly increased mtDNA damage in C57 mice, whereas damage was not significantly increased in the C3H mouse.

Figure 12:
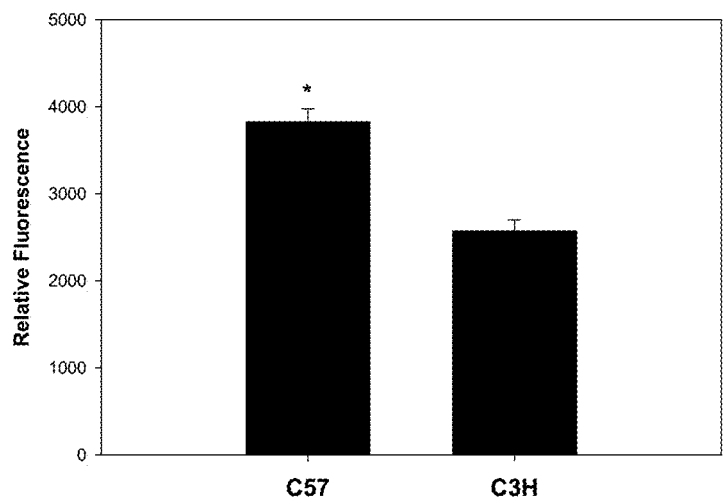
FIG. 12 shows relative levels of Amplex Red fluorescence from mitochondria isolated from C57 and C3H mouse aortas. 10-week old male C57 and C3H mice were sacrificed, and mitochondria isolated from aortas (2 aortas were pooled/sample). 50 Tg of mitochondrial protein were incubated with glutamate/malate, ADP, Amplex Red, and HRP. Relative fluorescence indicates increased oxidant production in C57 mitochondria relative to C3H. Asterisks (*) indicate significant differences (P<0.05) exist. N=6 mice, or 3 samples (C57); N=6 mice, or 3 samples (C3H).

To determine whether differences in oxidant levels existed between mitochondria from C57 and C3H mice, isolated mitochondria were assessed for oxidant generation by Amplex Red fluorescence (in the presence of HRP, reacts with $H_2O_2$). FIG. 12 shows that C57 mitochondria exhibited significantly higher levels of fluorescence compared to C3H mitochondria, consistent with increased oxidant production.

Increased levels of SOD2 or uncoupling proteins (UCPs) could explain, in part, the observed differences between C3H and C57 mitochondria. To determine whether differences in SOD2 protein or enzymatic activity or UCP levels existed, SOD2 activity and protein levels were assessed, as were UCP 2 and 3 transcript levels (RT-PCR) from aortas and hearts from 10-week old C57 and C3H mice. No differences were found, suggesting that the differences between C57 and C3H mice were not due to changes in SOD2 or UCP 2 or 3 levels.

Figure 13:
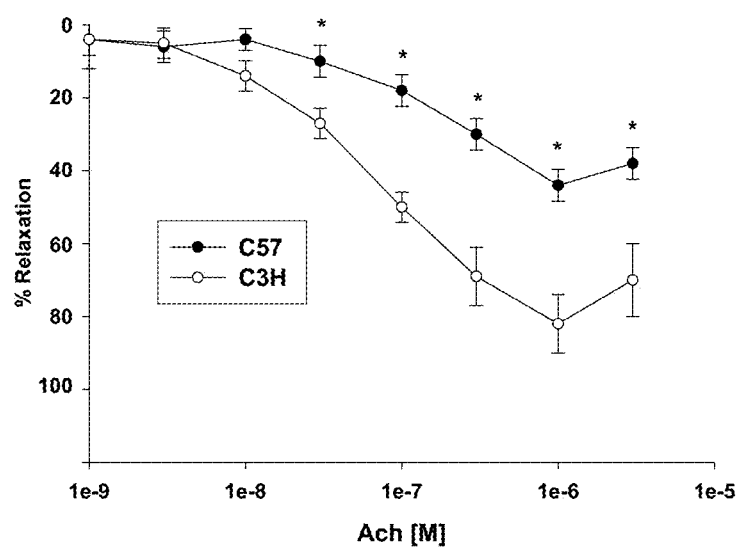
FIG. 13 shows isometric tension measured in aortic segments from 12-week old male C57 and C3H mice. Briefly, thoracic aorta were cut into 2 mm ring segments and suspended from a force-displacement transducer in an isolated tissue bath. To assess endothelium-dependent, NO-mediated relaxation, indomethacin-treated rings were contracted with phenylephrine followed by addition of acetylcholine. Relaxation was quantified as percent decrease in vessel tension of the pre-existing tone generated by phenylephrine. Data are the mean from 3-4 ring segments from each animal (N=4 mice/group). Asterisks (*) indicate significant difference (P<0.05) between the two mouse strains.

Because data suggested that C57 mitochondria were more tightly coupled than C3H, and that higher oxidant production (presumably $O_2$) appeared to be associated with C57 mitochondria, it was hypothesized that endothelial dependent vasorelaxation would be inhibited in C57 mice relative to C3H mice (due to increased oxidant stress). FIG. 13 shows that C3H mice were more sensitive to acetylcholine induced vasorelaxation, consistent with the principal that these animals had greater NO bioavailability by virtue of decreased mitochondrial oxidant production.

Figure 14A:
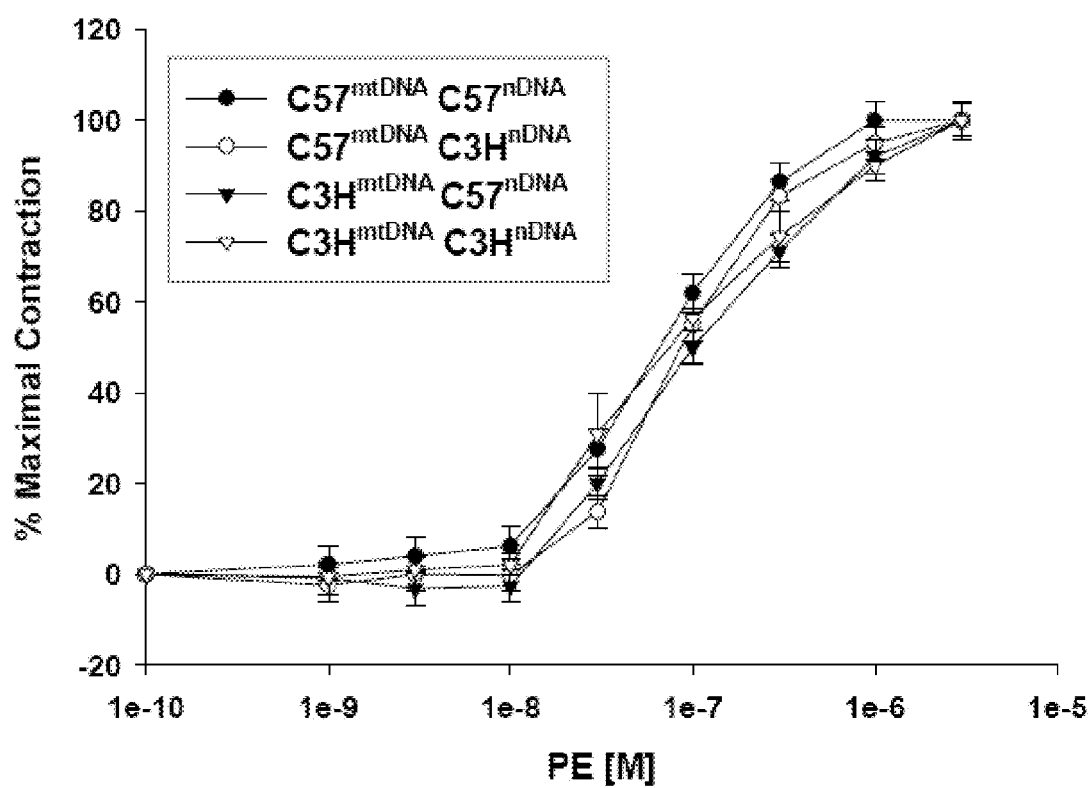
FIGS. 14A, 14B and 14C are graphs showing isometric tension measured in aortic segments from 14-week old male $C57^{mtDNA}/C57^{nDNA}$; $C3H^{mtDNA}/C3H^{nDNA}$; $C3H^{mtDNA}/C57^{nDNA}$; and $C57^{mtDNA}/C3H^{nDNA}$ mice. To assess endothelium-dependent, NO-mediated relaxation, indomethacin-treated rings were contracted with phenylephrine (PE) (FIG. 14A) followed by addition of acetylcholine (Ach) (FIG. 14B). Sodium nitroprusside (SNP) was added to contracted rings to determine endothelial independent relaxation (FIG. 14C). Relaxation was quantified as percent decrease in vessel tension of the pre-existing tone generated by PE. Data are the mean from 3-4 ring segments from each animal (N=3 mice/group). Asterisks (* and **) indicate significant difference (P<0.05) between the $C57^{mtDNA}/C57^{nDNA}$ and $C57^{mtDNA}/C3H^{nDNA}$, respectively.
Figure 14B:
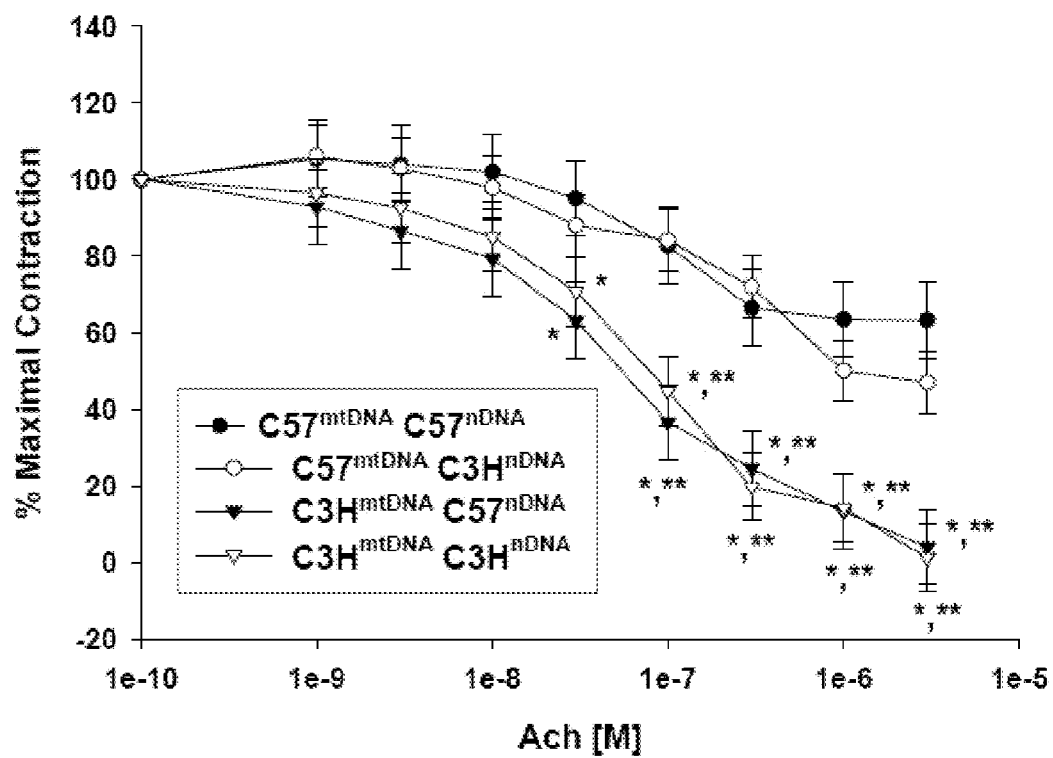
Figure 14C:
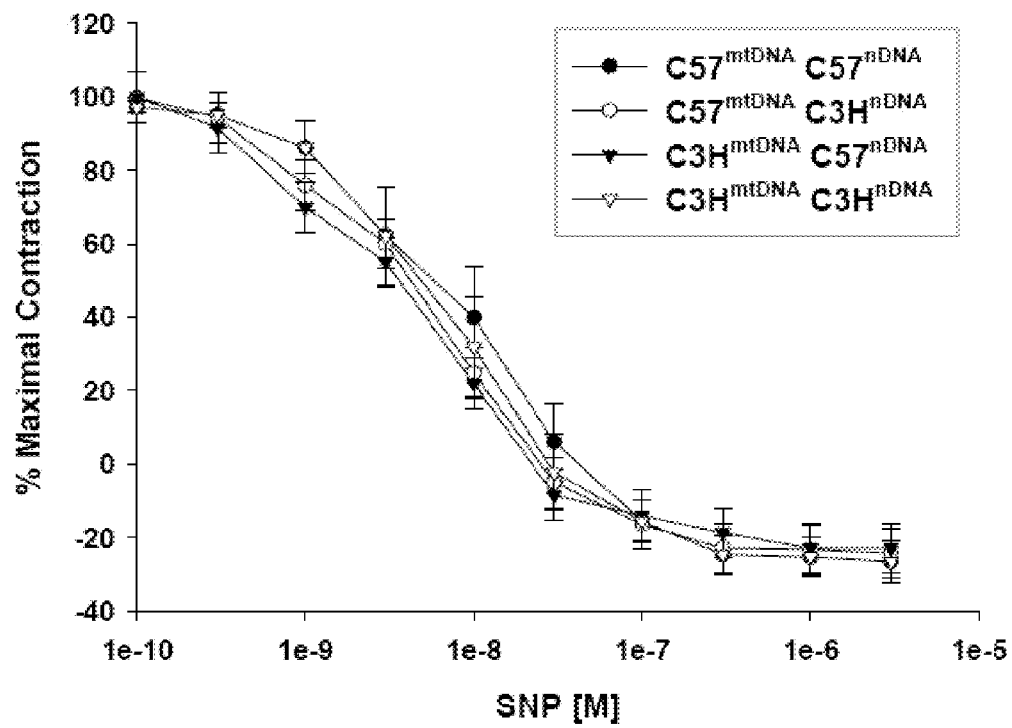

FIGS. 14A, 14B and 14C show that vascular function segregates with mitochondrial haplotype in mitochondrial-nuclear exchange mice. To evaluate the impact the mitochondrial genetic background on vascular function, 14 week old mitochondrial-nuclear exchange male $C3H^{mtDNA}/C57^{nDNA}$ and $C57^{mtDNA}/C3H^{nDNA}$ mice were used in vessel relaxation studies and compared to age-matched wild-type C57BL/6 ($C57^{mtDNA}/C57^{nDNA}$) and C3H/HeN ($C3H^{mtDNA}/C3H^{nDNA}$) male mice. FIGS. 14A, 14B and 14C show that while all groups responded to PE induced vessel contraction equally (FIG. 14A), significant differences in endothelial dependent vessel relaxation occurred between groups, with relaxation segregating with mtDNA haplotype (FIG. 14B). No significant differences were observed in endothelial independent vessel relaxation (FIG. 14C). These data support the notion that the mtDNA haplotype can contribute significantly to endothelial dependent vessel function, and moreover, are consistent with the hypothesis that mitochondrial function and genetics are important factors in influencing individual CVD susceptibility.

Figure 15:
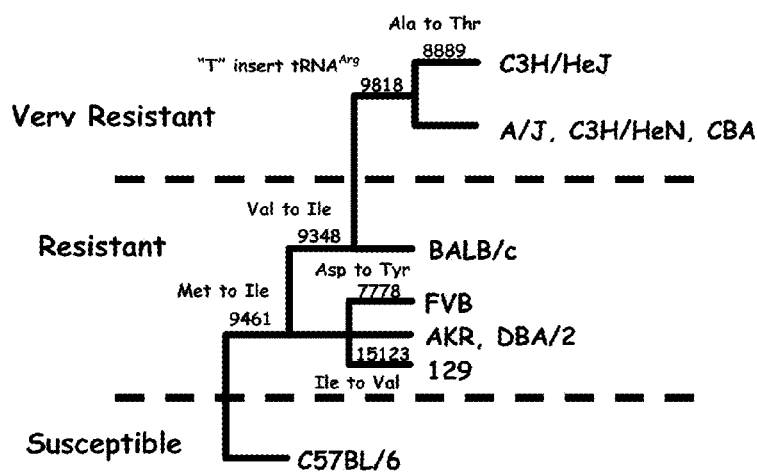
FIG. 15 shows mtDNA phylogeny derived from known mtDNA sequences from mice (GenBank) also known to have differential susceptibility to cardiovascular disease (CVD). CVD susceptibility is characterized as "Very Resistant," "Resistant," and "Susceptible" based upon review of the literature; "very resistant" indicates no atherosclerotic lesion formation, "resistant" indicates modest lesion formation relative to the "susceptible" C57 mouse. Amino acid or tRNA changes are indicated next to the location of each mtDNA mutation.

Based upon their known mtDNA sequences, phylogenetic analyses were performed to determine the potential phylogenetic relationships among strains of mice that were known to have different susceptibilities to CVD development. FIG. 15 shows a mtDNA phylogeny with indication of relative CVD susceptibilities (susceptible, resistant, very resistant) for each strain of mouse. The mtDNA phylogenetic relationships appear to reflect the relative susceptibility to CVD development, consistent with the hypothesis that mitochondrial genetics plays a role in CVD susceptibility.

In summary, these data collectively show that the CVD resistant C3H/HeN mouse has mitochondrial characteristics that make it less susceptible to cardiovascular disease. Further, these studies show that mitochondrial function and genetics are important factors in influencing individual CVD susceptibility.

What is claimed is:

1. A method for producing a mitochondrial-nuclear exchanged non-human animal, the method comprising:
    (a) selecting a non-human animal susceptible to a disease or disorder;
    (b) selecting a non-human animal that is not susceptible to the disease or disorder;
    (c) harvesting a pro-nuclear embryo from each of the non-human animals of steps (a) and (b);
    (d) enucleating the embryos of step (c);
    (e) transferring the nucleus from the embryo of the non-human animal that is not susceptible to the disease or disorder to the enucleated embryo of the non-human animal susceptible to the disease or disorder to make a resulting embryo, wherein the resulting embryo has mtDNA from the non-human animal susceptible to the disease or disorder and the nDNA from the non-human animal that is not susceptible to the disease or disorder; and
    (f) transferring the resulting embryo into an appropriate host and allowing the transferred embryo to develop into a progeny non-human animal, wherein the progeny non-human animal is a mitochondrial-nuclear exchanged non-human animal.

2. The method of claim 1, wherein the non-human animal that is not susceptible to the disease or disorder is from a wild-type non-human animal or a non-human animal resistant to the disease or disorder.

3. The method of claim 1, further comprising selecting a female mitochondrial-nuclear exchanged non-human animal.

4. A method of generating progeny of the female mitochondrial-nuclear exchanged non-human animal of claim 3 by crossing the female mitochondrial exchanged non-human animal with a knockout non-human animal, wherein the knockout non-human animal comprises a mutation in at least one gene associated with the disease or disorder such that the gene is not expressed or the protein expressed by the gene is not functional.

5. The method of claim 4, further comprising selecting progeny non-human animals of the cross that comprise mtDNA from the mitochondrial-nuclear exchanged non-human animals and nDNA from the knockout non-human animal.

6. The method of claim 1, wherein the disease or disorder is selected from the group consisting of cancer, cardiovascular disease, diabetes, neurological disorder, aging, metabolic disorder, immune disorder, obesity, and musculoskeletal disorder.

7. A mitochondrial-nuclear exchanged non-human animal made by the method of claim 1.

* * * * *

UNITED STATES PATENT AND TRADEMARK OFFICE
CERTIFICATE OF CORRECTION

PATENT NO. : 9,592,306 B2  
APPLICATION NO. : 14/697243  
DATED : March 14, 2017  
INVENTOR(S) : Scott Webster Ballinger et al.

Page 1 of 1

It is certified that error appears in the above-identified patent and that said Letters Patent is hereby corrected as shown below:

In the Specification

Column 1, Lines 18-20, Delete:
"This invention was made with government support under Grant No. W91XWH-07-1-0540 awarded by the Department of Defense. The government has certain rights in the invention."

And Insert:
-- This invention was made with government support under Grant No. W81XWH-07-1-0540 awarded by the Department of Defense. The government has certain rights in the invention. --

Signed and Sealed this  
First Day of June, 2021

Drew Hirshfeld  
*Performing the Functions and Duties of the*  
*Under Secretary of Commerce for Intellectual Property and*  
*Director of the United States Patent and Trademark Office*